US011166940B2

(12) United States Patent
Weisbrod et al.

(10) Patent No.: US 11,166,940 B2
(45) Date of Patent: Nov. 9, 2021

(54) TREATMENT OF CARDIAC DISORDERS BY BLOCKING SK4 POTASSIUM CHANNEL

(71) Applicant: Ramot at Tel-Aviv University Ltd., Tel-Aviv (IL)

(72) Inventors: David Weisbrod, Tel-Aviv (IL); Bernard Attali, Rehovot (IL); Asher Peretz, Kfar-Saba (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 187 days.

(21) Appl. No.: 15/850,000

(22) Filed: Dec. 21, 2017

(65) Prior Publication Data

US 2018/0177764 A1 Jun. 28, 2018

Related U.S. Application Data

(60) Provisional application No. 62/437,783, filed on Dec. 22, 2016.

(51) Int. Cl.
```
A61K 31/4174    (2006.01)
A61P 9/06       (2006.01)
G01N 33/50      (2006.01)
```

(52) U.S. Cl.
CPC .......... *A61K 31/4174* (2013.01); *A61P 9/06* (2018.01); *G01N 33/502* (2013.01); *G01N 33/5044* (2013.01); *G01N 33/5061* (2013.01)

(58) Field of Classification Search
CPC ..... A61K 31/4174; A61P 9/06; G01N 33/502; G01N 33/5061; G01N 33/5044
See application file for complete search history.

(56) References Cited

U.S. PATENT DOCUMENTS

2008/0090794 A1* 4/2008 Dinsmore ............ C07D 213/30
                                                        514/210.2
2009/0306159 A1    12/2009 Wulff et al.

OTHER PUBLICATIONS

Mayo Clinic Health Letter, Sick sinus syndrome, Sep. 2018 downloaded online Aug. 29, 2019. (Year: 2018).*
Agarwal et al., Agarwal JJ, Zhu Y, Zhang Q-Y, Mongin AA, Hough LB (2013) TRAM-34, a Putatively Selective Blocker of Intermediate-Conductance, Calcium-Activated Potassium Channels, Inhibits Cytochrome P450 Activity, PLoS ONE 8(5): e63028, May 7, 2013. (Year: 2013).*
Kim et al., Mechanism of automaticity in cardiomyocytes derived from human induced pluripotent stem cells, Journal of Molecular and Cellular Cardiology 81 (2015) 81-93, available online Jan. 30, 2015. (Year: 2015).*
Bueno et al. "Intermediate Calcium Activated Potassium Channels Sk4 Play a Role in the Acemaker Activity of Human Embryonic Stem Cell-Derived Cardiomyocytes and of the Murine Sinoatrial Node", Poster Presentation at the ISPP meeting Tel Aviv 2016 , 1 page.
Faggioni et al. "Sinus Node Dysfunction in Catecholaminergic Polymorphic Ventricular Tachycardia—Risk Factor and Potential Therapeutic Target?", Trends in Cardiovascular Medicine, 24(7): 273-278, 2014.
Glukhov et al. "Calsequestrin 2 Deletion Causes Sinoatrial Node Dysfunction and Atrial Arrhythmias Associated with Altered Sarcoplasmic Reticulum Calcium Cycling and Degenerative Fibrosis within the Mouse Atrial Pacemaker Complex", European Heart Journal, 36: 686-697, 2015.
Haron-Khun et al. "SK4 K+ Channels Regulate Cardiac Pacemaker in Sinoatrial Node and Their Blockade Ameliorate Arrhythmias in CPVT2 Patient-Derived iPSC and In Vivo in CASQ2 Knock-In and Knock-Out Mice", Poster Presentation at the ISPP meeting Tel Aviv 2016 , 1 page.
Haron-Khun et al. "SK4 K+ Channels Are Therapeutic Targets for the Treatment of Cardiac Arrhythmias", EMBO Molecular Medicine, 9: 415-429, 2017.
Itzhaki et al. "Modeling of Catecholaminergic Polymorphic Ventricular Tachycardia with Patient-Specific Human-Induced Pluripotent Stem Cells", Journal of the American College of Cardiology, 60(11): 990-1000, 2012.
Ju et al. "Blockade of KCa3.1 Attenuates Left Ventricular Remodeling after Experimental Myocardial Infarction", Cellular Physiology and Biochemistry, 36: 1305-1315, 2015.
Katz et al. "Optimizing Catecholaminergic Polymorphic Ventricular Tachycardia Therapy in Calsequestrin-Mutant Mice", Heart Rhythm, 7(11): 1676-1682, 2010.
Leenhardt et al. "Catecholaminergic Polymorphic Ventricular Tachycardia in Children", Circulation, 91: 1512-1519, 1995.
Neco et al. "Paradoxical Effect of Increased Diastolic Ca(2+) Release and Decreased Sinoatrial Node Activity in a Mouse Model of Catecholaminergic Polymorphic Ventricular Tachycardia", Circulation, 126: 392-401, 2012.
Novak et al. "Cardiomyocytes Generated from CPVTD307H Patients are Arrhythmogenic in Response to Beta-Adrenergic Stimulation", Journal of Cellular and Molecular Medicine, 16(3): 468-482, 2012.
Novak et al. "Functional Abnormalities in iPSC-Derived Cardiomyocytes Generated from CPVT1 and CPVT2 Patients Carrying Ryanodine or Calsequestrin Mutations", Journal of Cellular and Molecular Medicine, 19(8): 2006-2018, 2015.
Postma et al. "Catecholaminergic Polymorphic Ventricular Tachycardia: RYR2 Mutations, Bradycardia, and Follow Up of the Patients", Journal of Medical Genetics, 42: 863-870, 2005.

(Continued)

*Primary Examiner* — Johann R Richter
*Assistant Examiner* — Nabila G Ebrahim

(57) ABSTRACT

Methods of inducing bradycardia (slowing a heart rate) in a subject in need thereof, treating a medical condition in which inducing bradycardia (slowing a heart rate) is desirable or beneficial in a subject in need thereof and/or treating a medical condition associated with cardiac arrhythmia, are provided. The methods are effected by blocking SK4 channel in SAN cell of the subject and/or by administering to the subject a therapeutically effective amount of a blocker of an SK4 channel. A method of identifying candidate compounds for treating an arrhythmic cardiac disorder, by identifying compounds that reduce a pacing rate of the SAN cells is also provided.

Figure 2A:

3 Claims, 13 Drawing Sheets
(12 of 13 Drawing Sheet(s) Filed in Color)

(56) References Cited

OTHER PUBLICATIONS

Weisbrod et al. "Mechanisms Underlying the Cardiac Pacemaker: the Role of SK4 Calcium-Activated Potassium Channels", Acta Pharmacologica Sinica, 37: 82-97, 2016.
Weisbrod et al. "SK4 Ca2+ Activated K+ Channel is a Critical Player in Cardiac Pacemaker Derived from Human Embryonic Stem Cells", PNAS USA, 110(18): E1685-E1694, 2013.
Wulff et al. "Endothelial Small- and Intermediate-Conductance KCa Channels: An Update on Their Pharmacology and Usefulness as Cardiovascular Targets", Journal of Cardiovascular Pharmacology 61(2): 102-112, 2013.
Wulff et al. "Therapeutic Potential of KCa3.1 Blockers: Recent Advances and Promising Trends", Expert Review of Clinical Pharmacology, 3(3): 385-396, 2010.
Haron-Khun et al. "SK4 K+ Channels Regulate Sinoatrial Pacemaker and their Blockade Ameliorate Arrhythmias in CPVT2 Patient-Derived IPSC and in vivo in CASQ2 Knock-In and Knock-Out Mice," Poster Presentation at the 60th Annual Meeting of the Biophysical-Society, Los Angeles, CA: Feb. 27-Mar. 2, 2016, p. 29a.

\* cited by examiner

FIG. 1A
FIG. 1B
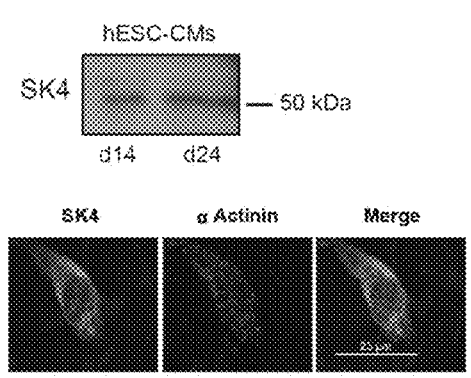
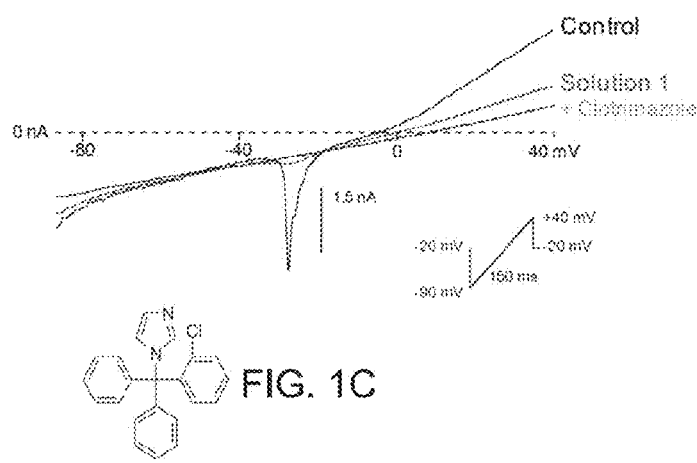
FIG. 1C
FIG. 1D
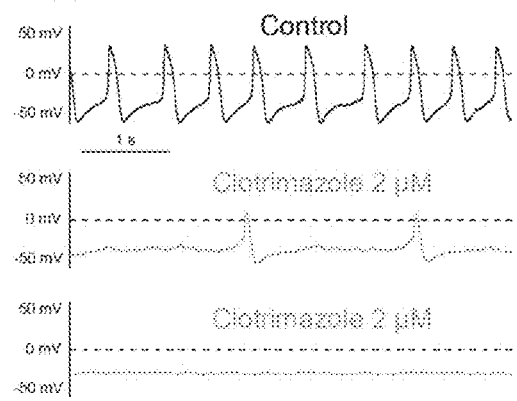
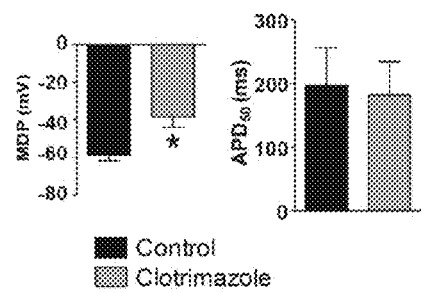

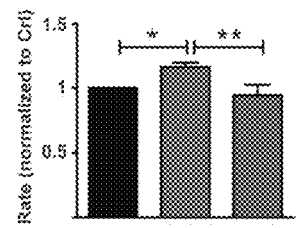
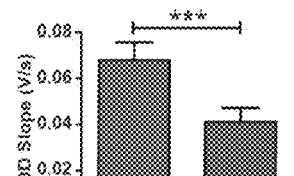
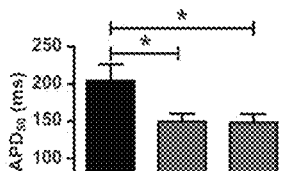

FIG. 6A
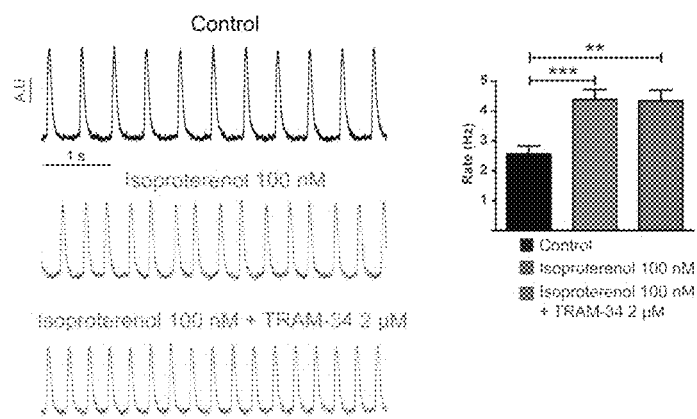
FIG. 6B
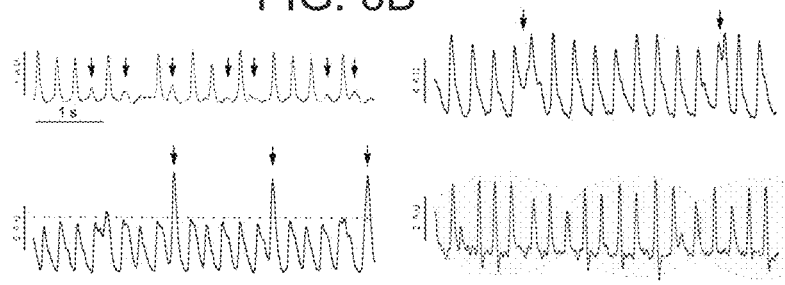
FIG. 6C
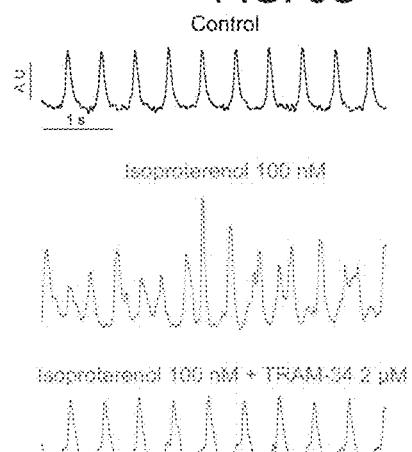
FIG. 6D
| n = 10 | Control | Isoproterenol | Isoproterenol + TRAM-34 |
|---|---|---|---|
| Local $Ca^{2+}$ release | 5 | 9 | 5 |
| Double humped transients | 0 | 4 | 0 |
| Large-stored released $Ca^{2+}$ waves | 1 | 4 | 0 |
| $Ca^{2+}$ alternans | 0 | 5 | 1 |

TREATMENT OF CARDIAC DISORDERS BY BLOCKING SK4 POTASSIUM CHANNEL

RELATED APPLICATION

This application claims the benefit of priority under 35 USC § 119(e) of U.S. Provisional Patent Application No. 62/437,783, filed Dec. 22, 2016, the contents of which are incorporated herein by reference in their entirety.

FIELD AND BACKGROUND OF THE INVENTION

The present invention, in some embodiments thereof, relates to therapy and, more particularly, but not exclusively, to methods of treating cardiac disorders, such as cardiac arrhythmia, and/or of inducing bradycardia, by blocking the $Ca^{2+}$-activated potassium channel SK4.

The cardiac sinoatrial node (SAN) pacemaker arises from its ability to generate a spontaneous and cyclical electric signal that is orchestrated by a cohort of different ion channels. The SAN pacemaker automaticity is essential for the proper heart contraction.

Proper function of the cardiac pacemaker is a critical feature of heart physiology. Around 75 times per minute, the sinoatrial node (SAN) produces different ionic currents. The result of those small currents is the generation of an electrical stimulation, which cyclically and regularly propagates through the conductive system (atrioventricular node, His bundles, Purkinje fibers) to the chambers (right and left auricles, right and left ventricles), leading to the heart contraction.

Currently known medications for treating cardiac arrhythmia include β1-adrenergic blockers (also known as β-blockers or beta blockers) and calcium ($Ca^{2+}$) channel blockers. While β1-adrenergic blockade is a very common strategy used for the treatment of several types of cardiopathies, including arrhythmia, the response to β-blockers often declines with time because of an "adrenergic escape" phenomenon (AE). For instance, between 31 to 39% of the patients suffering from chronic heart failure develop AE (see, Frankenstein L et al., Eur J Heart Fail. 2009). $Ca^{2+}$ channel blockers, although very effective in mice, have a limited benefit in humans, even when combined with β-blockers.

While the SAN has been discovered more than a century ago, the molecular mechanism of the "pacemaker ionic currents" remains highly controversial and debated.

For ethical reasons, studies on SAN cells have been performed mostly in small animals (rodents, rabbits), which display very different cardiac characteristics compared with human (higher heart rhythm, different calcium regulations or protein kinetics).

KCa3.1 blockers such as clotrimazole, the structurally related TRAM-34, and others, have been described in the art as potential candidates for treating a variety of conditions, including, for example, sickle cell anemia, asthma, autoimmune and cardiovascular diseases. TRAM-34 was shown to prevent MOG induced autoimmune encephalomyelitis, anti-collagen antibody induced arthritis, and trinitrobenzene sulfonic acid-induced colitis in mice, renal fibrosis following unilateral ureteral obstruction in mice and rats, angiogenesis in the mouse matrigel plug assay, atherosclerosis development in ApoE−/− mice 84, as well as angioplasty induced intimal smooth muscle hyperplasia (restenosis) in rats and pigs. KCa3.1 blockade has further been found to reduce microglia activation and thus curb inflammatory responses and reduce neuronal damage in models of ischemic stroke, traumatic brain injury, optic nerve transection, and traumatic spinal cord injury. KCa3.1 has been recognized in the art as an attractive pharmacological target for indications such as post-angioplasty restenosis, atherosclerosis, inflammatory bowel disease, autoimmune encephalomyelitis, immunosuppression and ischemic stroke. See, for example, reviews by Wulff et al. in J Cardiovasc Pharmacol. 2013 February; 61(2): 102-112. doi:10.1097/FJC.0b013e318279ba20; and in Expert Rev Clin Pharmacol. 2010 May; 3(3): 385-396.

Weisbrod et al., in Proc Natl Acad Sci USA 110, E1685-1694 (2013), investigated the cardiac pacemaker process in human embryonic stem cells-derived cardiomyocytes (hESC-CMs), a cellular model which mimics the cardiac cells of the primitive heart during development. In those cells, the currents involved in the pacemaker mechanism were investigated, and, using biochemical, electrophysiological and pharmacological techniques, the intermediate $Ca^{2+}$-activated potassium channel ($IK_{Ca}$/SK4, KCa3.1) was identified as a target in the heart pacemaker mechanism (see, Background Art FIGS. 1A-D, further discussed hereinafter).

Catecholaminergic polymorphic ventricular tachycardia (abbreviated herein throughout and in the art as CPVT) is an inherited arrhythmogenic syndrome characterized by physical or emotional stress-induced polymorphic ventricular tachycardia in otherwise structurally normal hearts with a high fatal event rate in untreated patients. CPVT comprises heterogeneous genetic diseases, including mutations in ryanodine receptor type 2 (RyR2), calsequestrin 2 (CASQ2), triadin or calmodulin5-11. The RyR2 mutations (CPVT1) are 'gain of function' mutations while CASQ2 mutants (CPVT2) are 'loss of function' mutations, which both lead to diastolic $Ca^{2+}$ leakage from the sarcoplasmic reticulum (SR). This eventually produces local increases in cytosolic $Ca^{2+}$ that is extruded via the $Na^+$—$Ca^{2+}$ exchanger NCX1 generating local depolarization with early- or delayed-after-depolarizations (EADs or DADs) that trigger premature beats and fatal polymorphic ventricular tachycardia.

Recent studies performed in human induced pluripotent stem cell-derived cardiomyocytes (hiPSC-CMs) from CPVT patients bearing mutations in either CASQ2 (D307H) or RyR2 (M4109R) showed that β-adrenergic stimulation caused marked elevation in diastolic $Ca^{2+}$, DADs and oscillatory prepotentials [Itzhaki, I., et al. *J Am Coll Cardiol* 60, 990-1000 (2012); Novak, A., et al. *J Cell Mol Med* 19, 2006-2018 (2015); and Novak, A., et al. *J Cell Mol Med* 16, 468-482 (2012)]. Sinus bradycardia was also consistently described in CPVT patients and in CPVT mouse models, suggesting that sinoatrial node (SAN) dysfunction may reflect another primary defect caused by CPVT mutations [Leenhardt, A., et al. *Circulation* 91, 1512-1519 (1995); Faggioni et al., *Trends Cardiovasc Med* 24, 273-278 (2014); Glukhov, A. V., et al. *Eur Heart J* 36, 686-697 (2015); Katz, G., et al. *Heart Rhythm* 7, 1676-1682 (2010); Neco, P., et al. *Circulation* 126, 392-401 (2012); and Postma, A. V., et al. *J Med Genet* 42, 863-870 (2005)].

Current therapies for CPVT are phenotype driven and include exercise prohibition and β1-adrenergic blockade. The options in unresponsive patients include additional drugs, primarily flecainide, or implanting a defibrillator (ICD) and sympathetic denervation.

Additional Background art includes U.S. Patent Application having Publication No. 2009/0306159; Ju et al., Cell Physiol Biochem (2015) 36:1305-1315; Weisbrod et al., Acta Pharmacologica Sinica (2016) 37: 82-97; Haron-Khun et al., Poster Presentation at the 60th Annual Meeting of the Biophysical-Society Location: Los Angeles, Calif. Date: Feb. 27-Mar. 2, 2016; Hanna Bueno et al., Poster Presentation at the 2016 ISPP meeting, Tel Aviv; Haron-Khun et al., Poster Presentation at the 2016 ISPP meeting, Tel Aviv; and Haron-Khun et al., EMBO Molecular Medicine (2017) 9, 415-429.

SUMMARY OF THE INVENTION

According to an aspect of some embodiments of the present invention there is provided a method of inducing bradycardia (e.g., slowing a heart rate) in a subject in need thereof, the method comprising administering to the subject a therapeutically effective amount of a blocker of an SK4 channel.

According to an aspect of some embodiments of the present invention there is provided a method of treating a medical condition in which inducing bradycardia (e.g., slowing a heart rate) is desirable or beneficial in a subject in need thereof, the method comprising blocking a SK4 channel in SAN cells of the subject.

According to some of any of the embodiments described herein, the blocking comprises administering to the subject a blocker of a SK4 channel.

According to an aspect of some embodiments of the present invention there is provided a method of treating a medical condition in which inducing bradycardia (e.g., slowing a heart rate) is desirable or beneficial in a subject in need thereof, the method comprising administering to the subject a blocker of a SK4 channel.

According to some of any of the embodiments described herein, the medical condition is associated with cardiac arrhythmia.

According to some of any of the embodiments described herein, the medical condition is a cardiac disease or disorder.

According to some of any of the embodiments described herein, the medical condition is an atrial disease or disorder (e.g., atrial arrhythmia).

According to some of any of the embodiments described herein, the medical condition is a ventricular disease or disorder (e.g., ventricular arrhythmia).

According to some of any of the embodiments described herein, the medical condition is CPVT.

According to an aspect of some embodiments of the present invention there is provided a method of treating arrhythmia, including atrial, ventricular and any other arrhythmia) in a subject in need thereof, the method comprising administering to the subject a blocker of a SK4 channel.

According to some of any of the embodiments described herein, the subject is a human subject.

According to some of any of the embodiments described herein, the subject is a post-natal subject.

According to some of any of the embodiments described herein, the SK-4 channel blocker forms a part of a pharmaceutical composition which further comprises a carrier.

Figure 11:
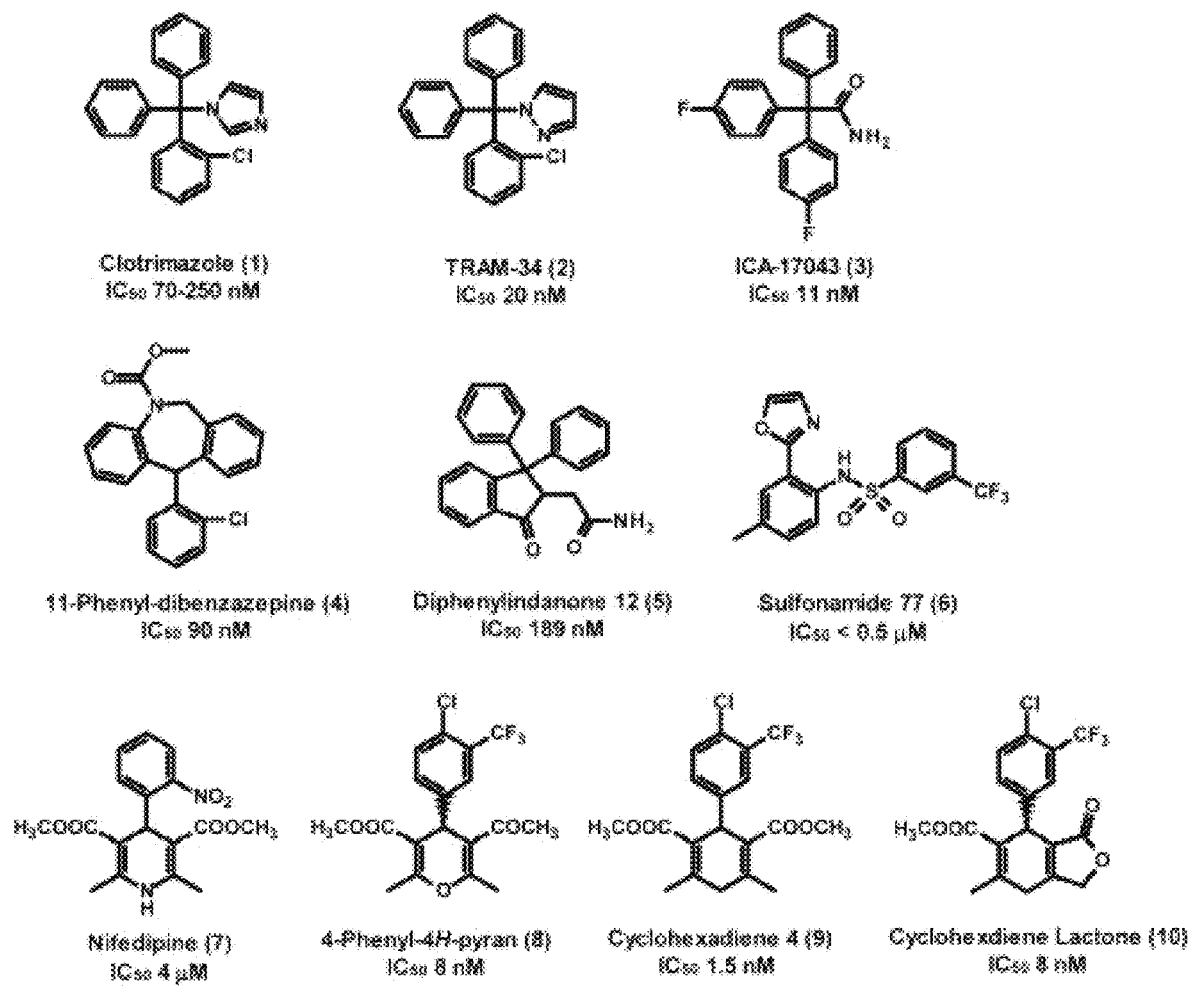

According to some of any of the embodiments described herein, the SK4 channel blocker is selected from the group consisting of clotrimazole, TRAM-34, Senicapoc, and any of the other SK4 channel blockers described herein (see, FIG. 11, for non-limiting examples).

According to an aspect of some embodiments of the present invention there is provided a method of identifying a candidate compound for treating an arrhythmic cardiac disorder, the method comprising:

contacting a compound identified as a blocker of SK4 potassium channel with SAN cells; and determining if the compound reduces a pacing rate of the SAN cells, wherein a compound that reduces a pacing rate of the SAN cells is identified as a candidate compound for treating an arrhythmic cardiac disorder.

According to some of any of the embodiments described herein, a compound is identified as a blocker of SK4 potassium channel by:

contacting the compound with cells expressing SK4 potassium channel; and determining if a SK4 current amplitude is reduced upon the contacting, wherein a compound that causes a reduction in the SK4 current amplitude upon the contacting is identified as a blocker of a SK4 channel.

According to some of any of the embodiments described herein, the cells expressing SK4 potassium channels are transfected cells ectopically expressing the channels.

According to some of any of the embodiments described herein, contacting the compound with the SAN cells is effected in vitro.

According to some of any of the embodiments described herein, the SAN cells are obtained from induced pluripotent stem cells-derived pacemaker cells and/or from a subject suffering from an arrhythmic cardiac disorder.

According to some of any of the embodiments described herein, a compound identified as a candidate compound for treating an arrhythmic disorder is administered to a subject suffering from an arrhythmic disorder to thereby determine an effect of the compound on a heart rate of the subject.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-D (Background Art) present data obtained in biochemical experiments revealing the existence of the SK4 protein on cardiomyocytes (FIG. 1A), with upper panel presenting a Western blot from young and older hESC-CMs lysates showing a 50 KDa band corresponding to the SK4 channel and lower panel presenting immunocytochemistry showing the expression of SK4 in green and the cardiac marker α-actinin in red in the same single hESC-CMs; electrophysiological characterization of the SK4 current in a single cardiac hESC-CM (FIG. 1B); the chemical structure of clotrimazole (FIG. 1C); and bar graphs showing the pharmacological effects of clotrimazole on the cardiac pacing, with the spontaneous electric activity of the cell recorded in the current clamp configuration of the patch clamp technique before (black trace) and during exposure to 2 μM clotrimazole (violet trace).

Figure 2B:
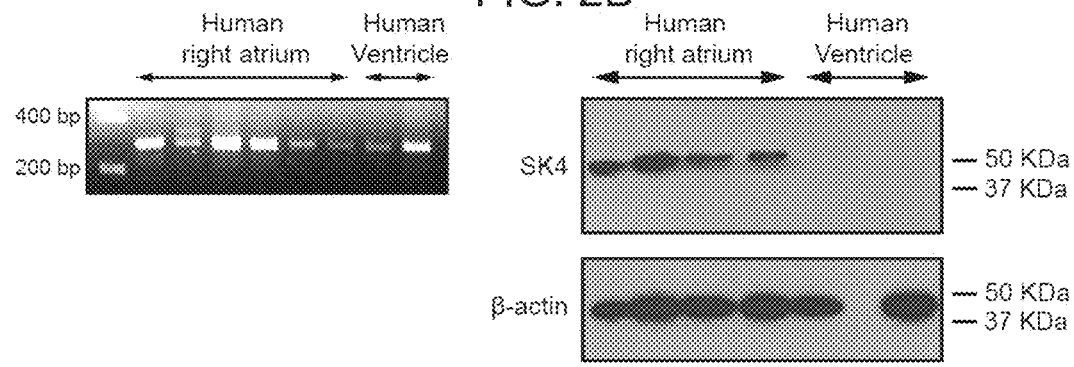
Figure 2C:
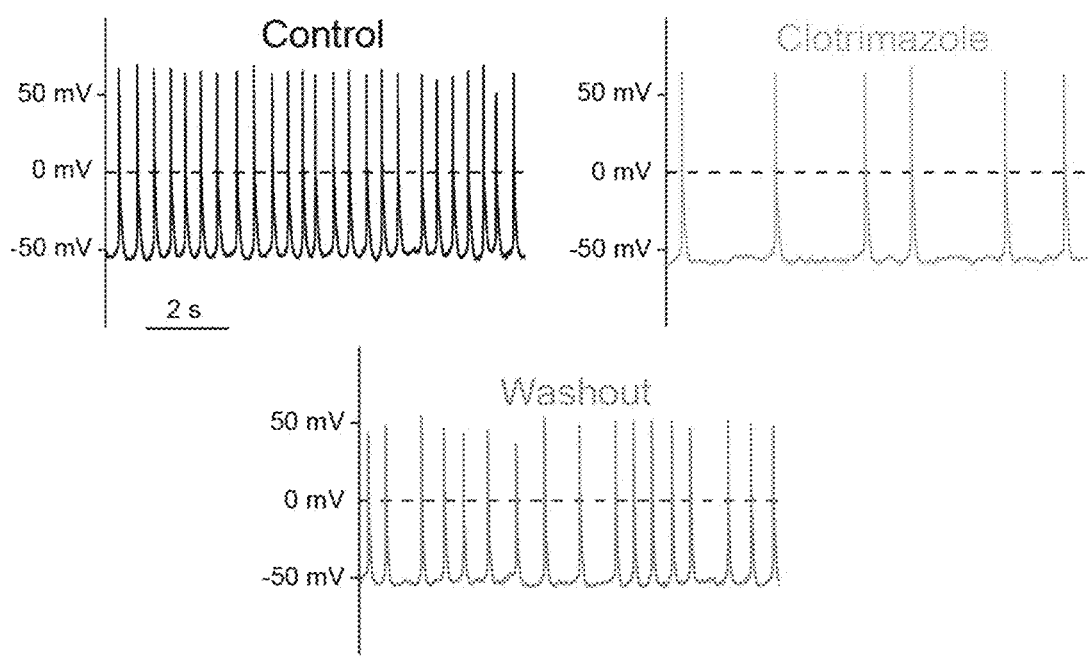

FIGS. 2A-C present data obtained in experiments conducted in mice heart samples and human heart biopsia from patients. FIGS. 2A and 2B present biochemical experiments revealing the existence of the SK4 channel on murine heart (FIG. 2A) and in human right atrium and ventricle biopsia (FIG. 2B). FIG. 2A, left panel, presents a reverse transcriptase PCR of the SK4 mRNA (SAN=sinoatrial node; RA=right appendage; LA=left appendage; RV=right ventricle, LV=left ventricle); and right panel presents Western blot on murine lysates from the same heart areas. FIG. 2B shows the presence of a SK4 channel at the transcript level (left panel), and at the protein level (right panel). FIG. 2C presents the pharmacological effects of clotrimazole on the pacemaker activity of SAN cells, by showing the spontaneous electric activity of the cell recorded in the current clamp configuration of the patch clamp technique before (black trace) and during (violet trace) exposure to 2 μM clotrimazole.

Figure 3A:
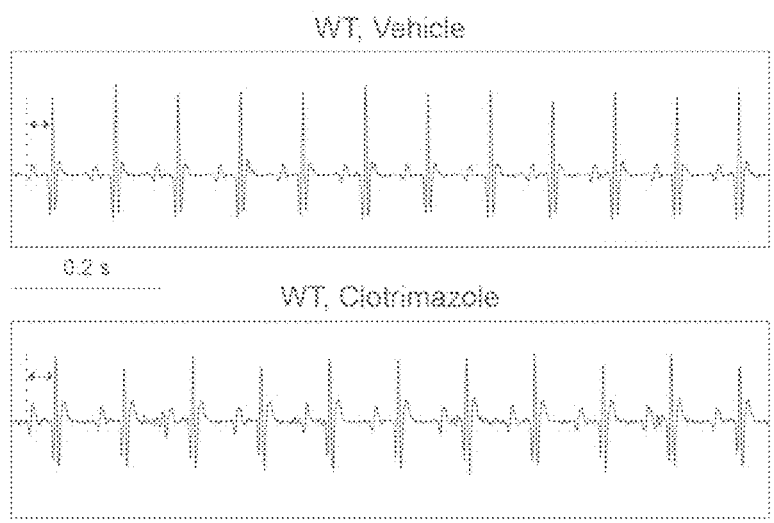
Figure 3C:
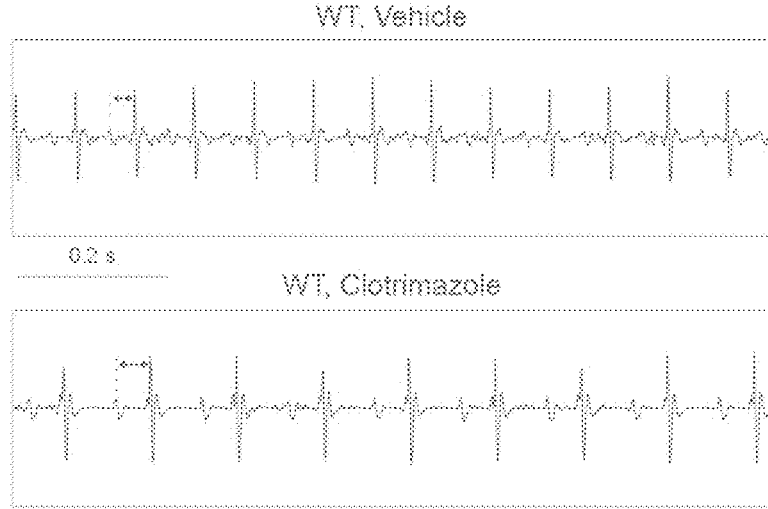
Figure 3B:
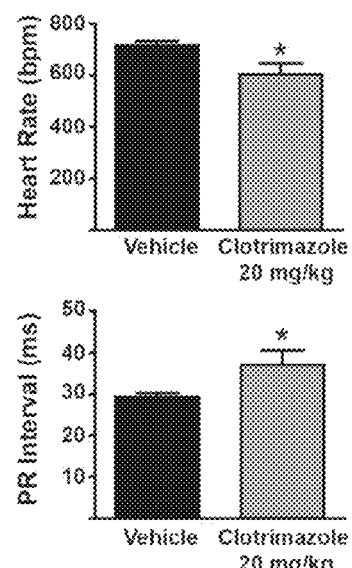
Figure 3D:
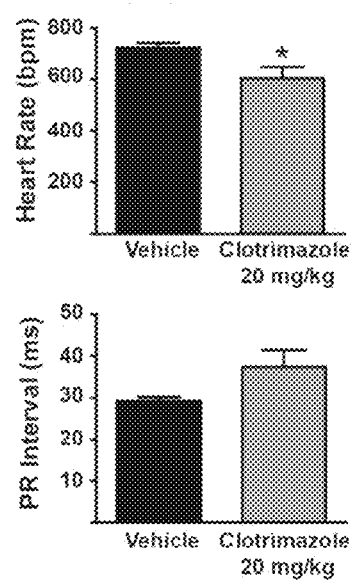

FIGS. 3A-D present representative ECG recording following intraperitoneal injection of vehicle (upper) and 20 mg/kg clotrimazole (lower) in norma mice at rest, with sequential vehicle and clotrimazole injections were performed on the same animal (FIG. 3A); data summary of heart rate at rest (upper; *P=0.0364, n=10) and PR interval (lower; *P=0.0437, n=10) (FIG. 3B); and representative ECG recording following intraperitoneal injection of vehicle (upper) and 20 mg/kg clotrimazole (lower) in mice following treadmill exercise (FIG. 3C); and data summary of heart rate at rest (upper) and PR interval (lower) (FIG. 3D).

Figure 4A:
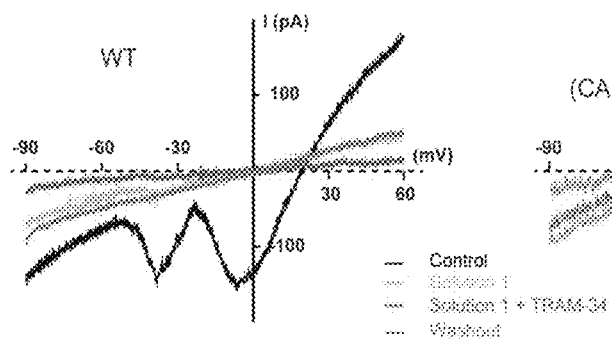
Figure 4B:
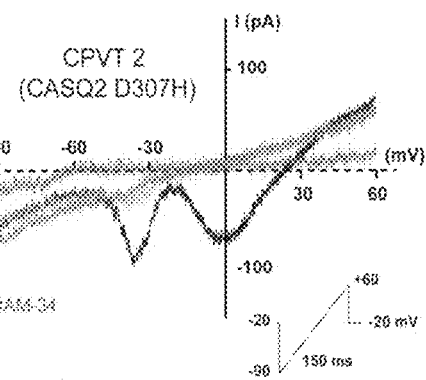
Figure 4C:
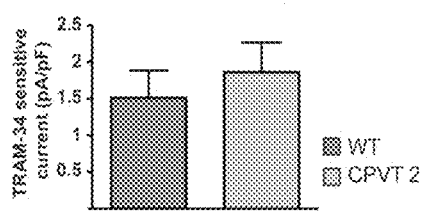
Figure 4D:
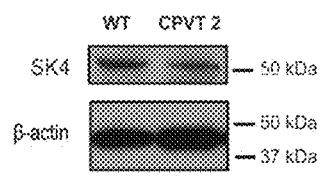
Figure 4E:
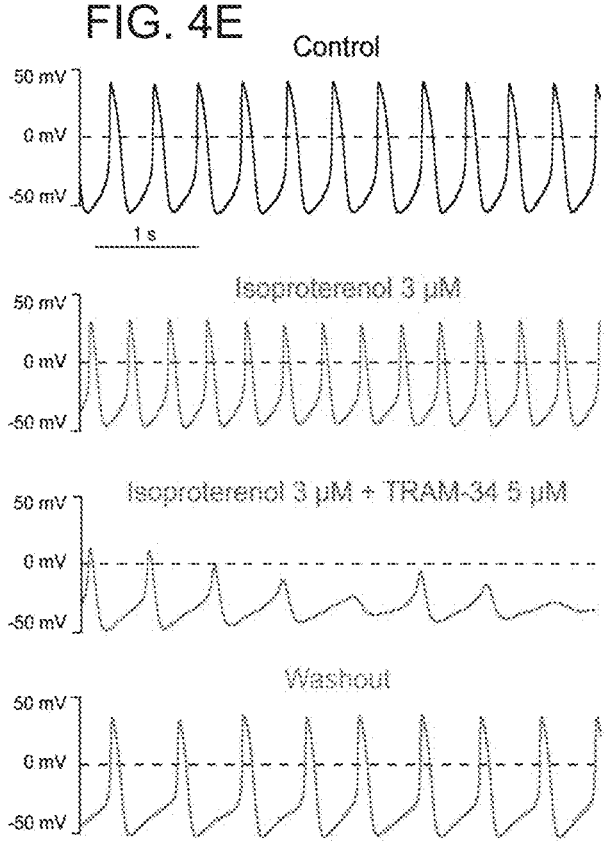

FIGS. 4A-G present representative traces of hiPS-CMs derived from normal (FIG. 4A) or CPVT2 (CASQ2 D307H) (FIG. 4B) patients, with Cells were held at −20 mV and a voltage ramp of 150 ms from −90 to +60 mV was applied, as shown in FIG. 2B; the TRAM-sensitive current calculated as a difference between the current density measured at +60 mV with solution 1 alone (orange trace) and solution 1+5 11M TRAM-34 (green trace) (n=7-9) (FIG. 4C); representative Western blots of beating EBs lysates from normal and CPVT2 (CASQ2 D307H) patients showing immuno-reactive SK4 protein (about 50 KDa) (FIG. 4D); representative traces of spontaneous APs recorded in hiPS-CM derived from a normal individual (FIG. 4E; Left) and bar graphs presenting data summary of pacing rate (FIG. 4E; Right); representative traces of spontaneous APs recorded in hiPS-CM derived from a CPVT2 (CASQ2 D307H) patients (FIG. 4F; Left); bar graphs showing data summary of pacing rate FIG. 4F (Right); and representative trace of a voltage-ramp protocol performed in cardiomyocytes derived from human embryonic stem cells before (black trace) and after applying 5 μM TRAM-34 (red trace) (FIG. 4G), with cells held at −20 mV and a voltage ramp of 150 ms from −90 to +60 mV was applied.

Figure 5A:
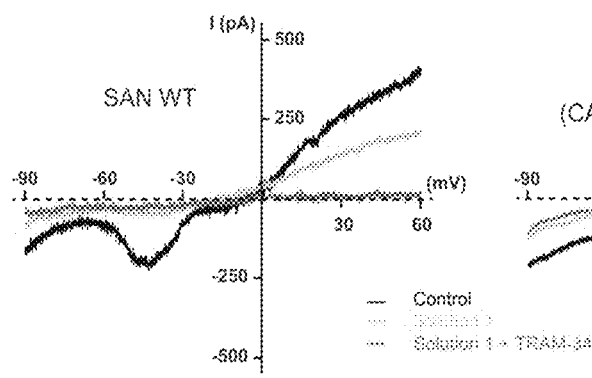
Figure 5B:
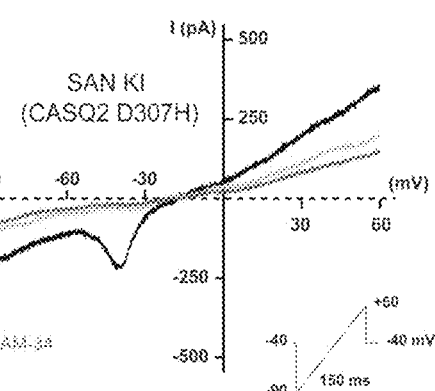
Figure 5C:
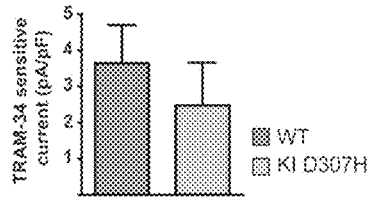
Figure 5D:
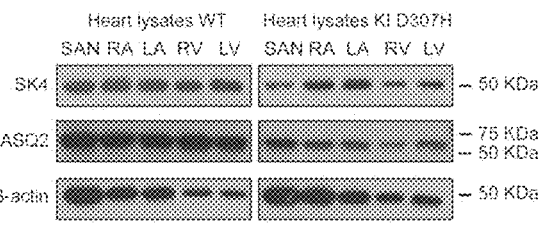
Figure 5E:
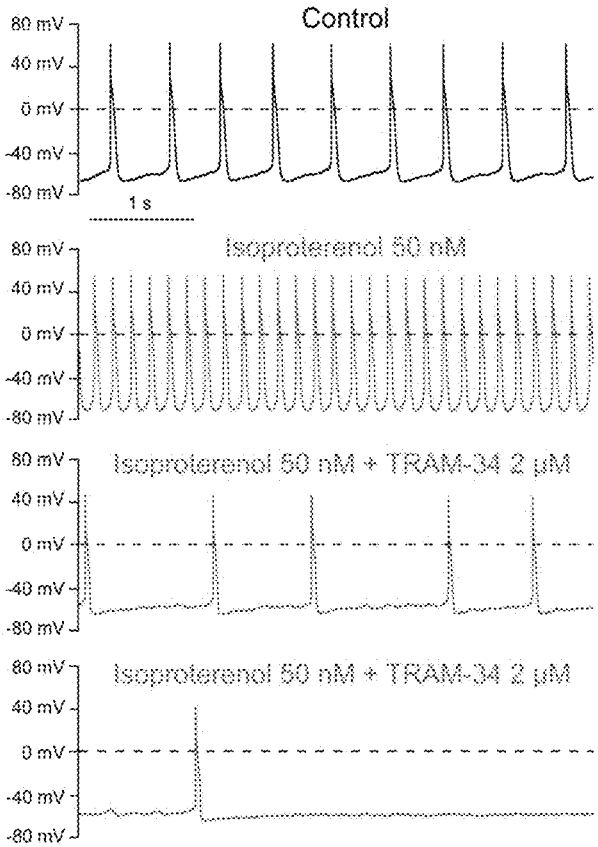

FIGS. 5A-F present representative traces of SAN cells isolated from WT (FIG. 5A) and CASQ2-D307H KI mice (FIG. 5B), with cells held at −40 mV and a voltage ramp of 150 ms from −90 to +60 mV was applied; the TRAM-sensitive current calculated as in FIG. 4C (n=8-12) (FIG. 5C); representative Western blots of SAN lysates from WT (left) and CASQ2-D307H KI (right) mice showing the immuno-reactive bands of SK4, CASQ2 and β-actin proteins in SAN, right and left atrial appendages, right and left ventricle (FIG. 5D); representative traces of spontaneous APs recorded in single SAN cell from WT mice (FIG. 5E; Left) and corresponding bar graphs showing data summary of pacing rate (FIG. 5E; Right); representative traces of spontaneous APs recorded in single SAN cell from CASQ2 D307H KI mice (FIG. 5F; Left) and corresponding bar graphs showing data summary of rate (n=6) (FIG. 5F; Right).

FIGS. 6A-D present representative traces of spontaneous calcium transients recorded ex vivo in intact SAN tissue preparations from WT mice (FIG. 6A; Left) and a corresponding data summary of calcium transient rate (FIG. 6A; Right); representative traces of different types of calcium transient abnormalities recorded in intact SAN from CASQ2 D307H KI mice, termed as "local $Ca^{2+}$ release" (FIG. 6B; upper left), "double humped transients" (FIG. 6B; upper right), "large-stored released $Ca^{2+}$ waves" (FIG. 6B; lower left) and "calcium alternans" (FIG. 6B; lower right); representative trace of spontaneous calcium transients recorded from intact SAN of CASQ2 D307H KI (FIG. 6C) and data summary of the arrhythmic calcium transients in SAN from CASQ2 D307H KI under baseline conditions, following exposure to 100 nM isoproterenol and 100 nM isoproterenol+2 μM TRAM-34 (FIG. 6D).

Figure 7A:
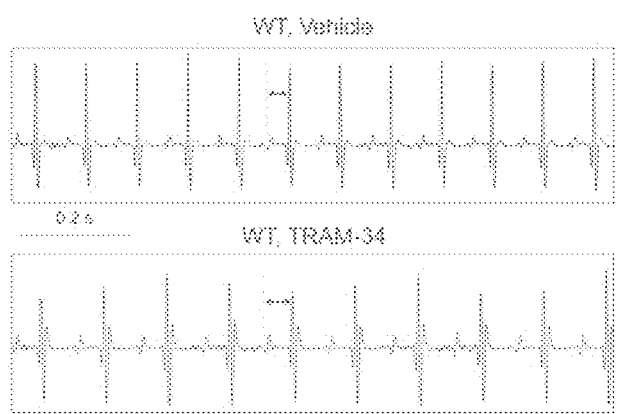
Figure 7B:
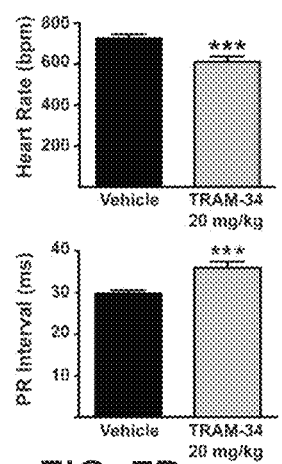
Figure 7C:
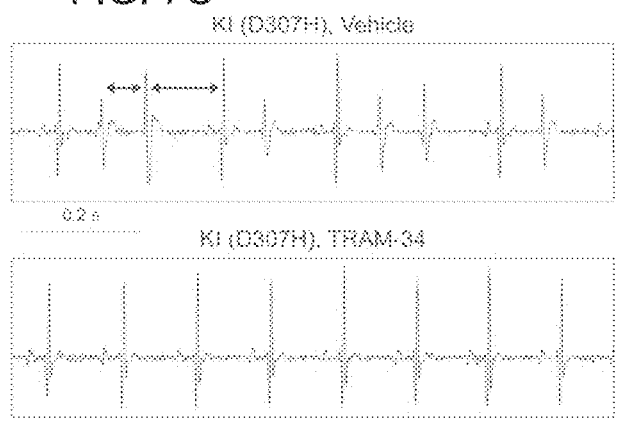
Figure 7D:
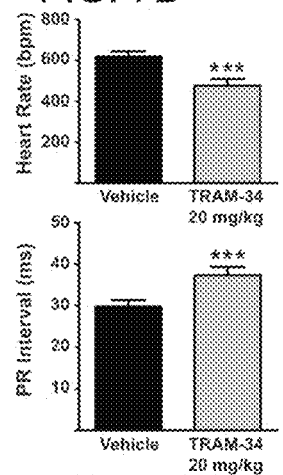
Figure 7E:
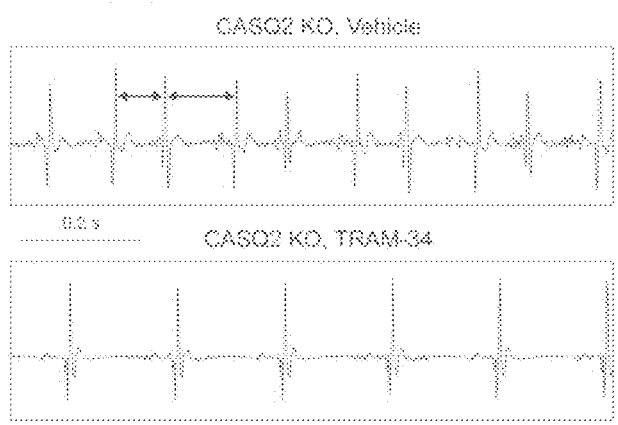
Figure 7F:
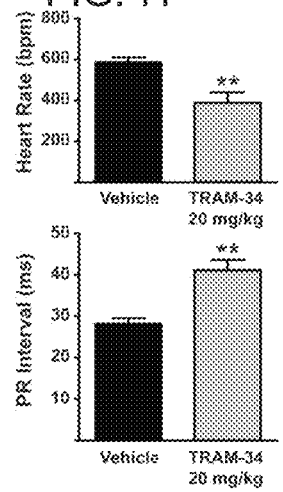

FIGS. 7A-F present representative ECG recording following intraperitoneal injection of vehicle (upper) and 20 mg/kg TRAM-34 (lower) in WT mice at rest (FIG. 7A) and corresponding data summary of heart rate (Paired t-test; *P=0.0003, n=10) and PR interval (Paired t test; *P=0.0004, n=10) in WT mice at rest (FIG. 7B); representative ECG recording following IP injection of vehicle (upper) and 20 mg/kg TRAM-34 (lower) in CASQ2-D307H KI mice at rest (FIG. 7C) and corresponding data summary of heart rate (Paired t-test; *P<0.0001, n=12) and PR interval (Paired t-test; *P=<0.0001, n=12) in CASQ2-D307H KI mice at rest (FIG. 7D); representative ECG recording following IP injection of vehicle (upper) and 20 mg/kg TRAM-34 (lower) in CASQ2 KO mice at rest showing that TRAM-34 produced similar effects as in CASQ2-D307H KI mice (FIG. 7E) and corresponding data summary of heart rate (Paired t-test; P=0.004, n=7 mice) and PR interval (Paired t-test; P=0.0041, n=7) in CASQ2 KO mice at rest (FIG. 7F).

Figure 8A:
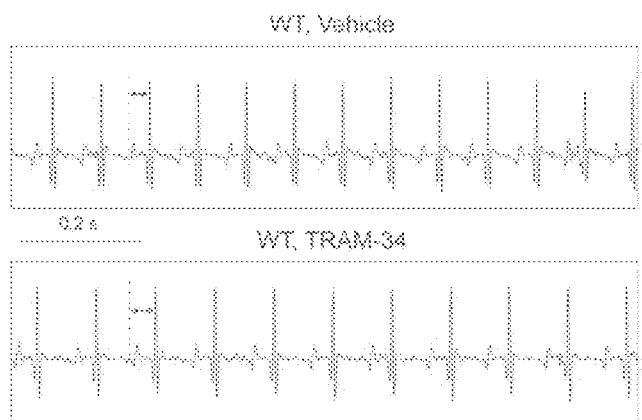
Figure 8B:
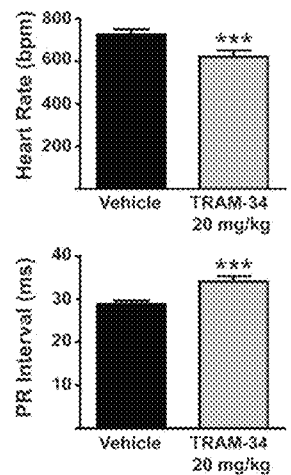
Figure 8C:
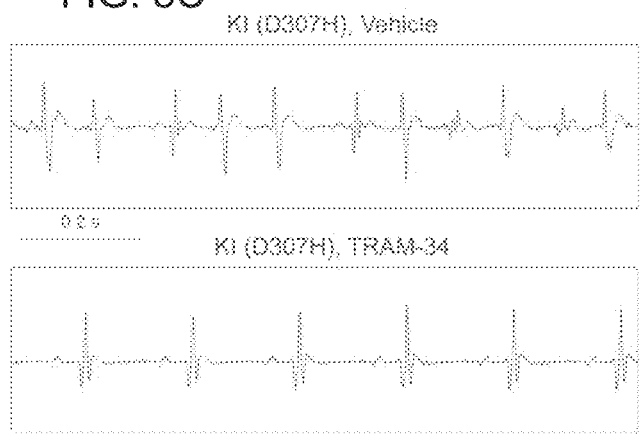
Figure 8D:
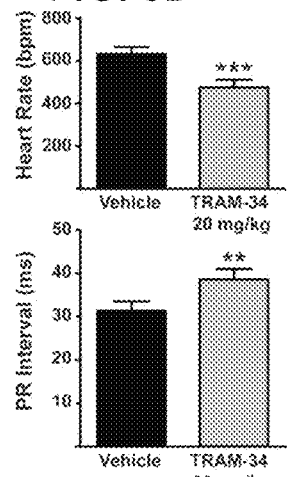
Figure 8E:
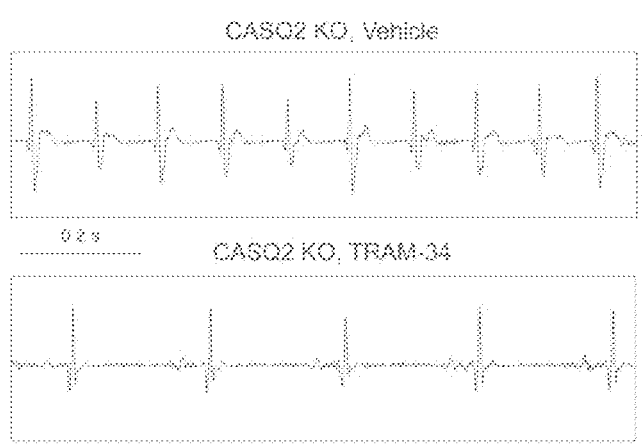
Figure 8F:
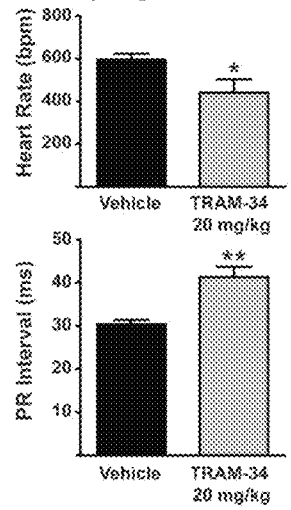

FIGS. 8A-F present representative ECG recording following intraperitoneal injection of vehicle (FIG. 8A; upper) and 20 mg/kg TRAM-34 (FIG. 8A; lower) in WT mice during treadmill exercise; and corresponding data summary of heart rate (Paired t-test; *P=0.001, n=10) and PR interval (Paired t-test; *P=0.0005, n=10) in WT mice during exercise (FIG. 8B); representative ECG recording following IP injection of vehicle (FIG. 8C; upper) and 20 mg/kg TRAM-34 (FIG. 8C; lower) in CASQ2-D307H KI mice during treadmill exercise; and corresponding data summary of heart rate (Paired t-test; *P=0.0004, n=11) and PR interval (Paired t-test; P=0.0099, n=9) in CASQ2-D307H KI mice during exercise (FIG. 8D); representative ECG recording following IP injection of vehicle (FIG. 8E; upper) and 20 mg/kg TRAM-34 (FIG. 8E; lower) in CASQ2 KO mice during exercise. Arrhythmias such as NSVT were suppressed by TRAM-34 injection; and corresponding data summary of heart rate (Paired t-test; *P=0.0165, n=7) and PR interval (Paired t-test; **P=0.0042, n=7) in CASQ2 KO mice during exercise (FIG. 8F).

Figure 9A:
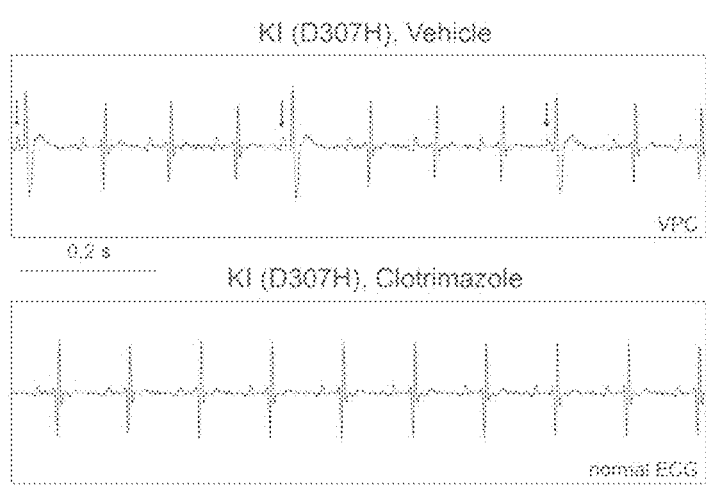
Figure 9B:
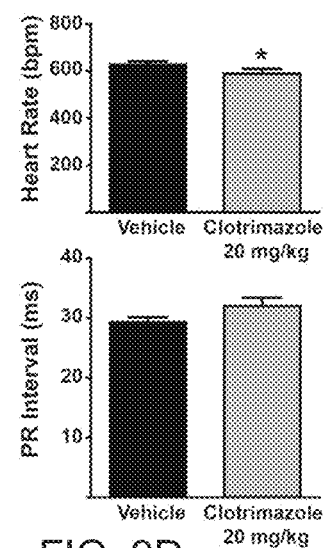
Figure 9C:
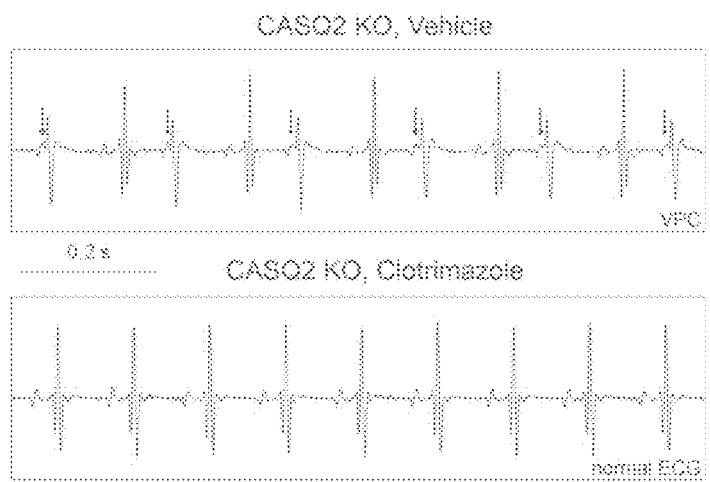
Figure 9D:
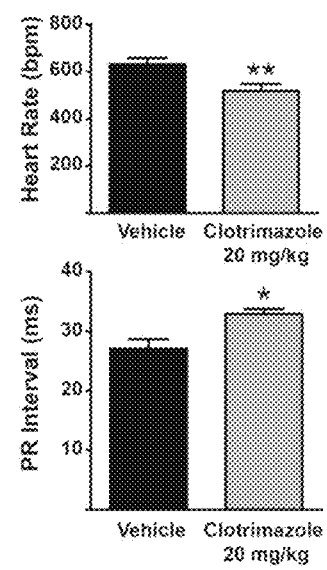

FIGS. 9A-D present representative ECG recording following IP injection of vehicle (FIG. 9A; upper) and 20 mg/kg clotrimazole (FIG. 9A; lower) in CASQ2-D307H KI mice at rest; and corresponding data summary of heart rate (Paired t-test; *P=0.0260, n=7) and PR interval (n=7) in CASQ2-D307H KI mice at rest (FIG. 9B); representative ECG recording following IP injection of vehicle (upper) and 20 mg/kg clotrimazole (FIG. 9C; lower) in CASQ2 KO mice at rest showing that clotrimazole produced similar effects as in CASQ2-D307H KI mice; and corresponding data summary of heart rate (Paired t-test; **P=0.0078, n=7) and PR interval (Paired t-test; *P=0.0111, n=7) in CASQ2 KO mice at rest (FIG. 9D).

Figure 10A:
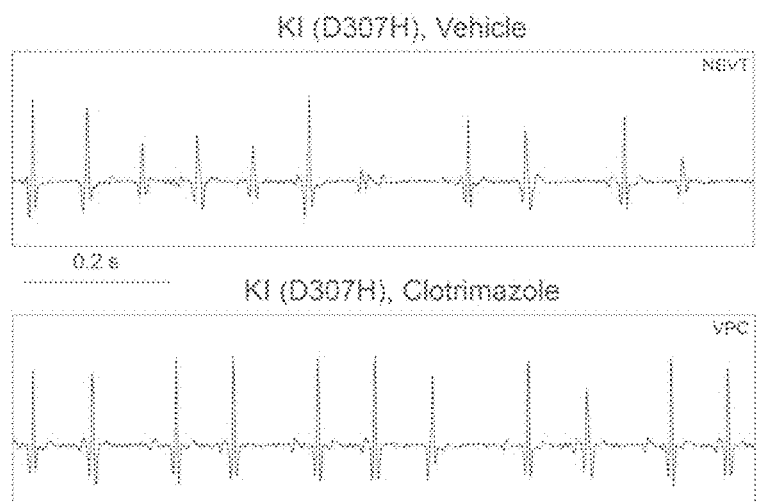
Figure 10B:
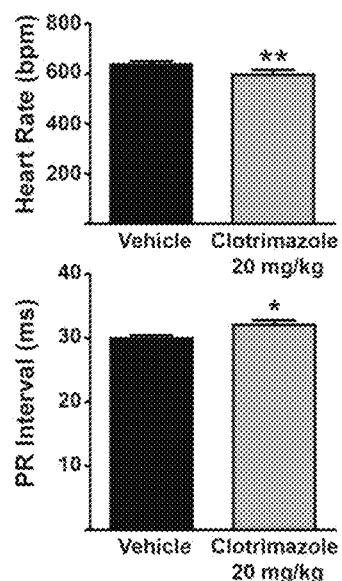
Figure 10C:
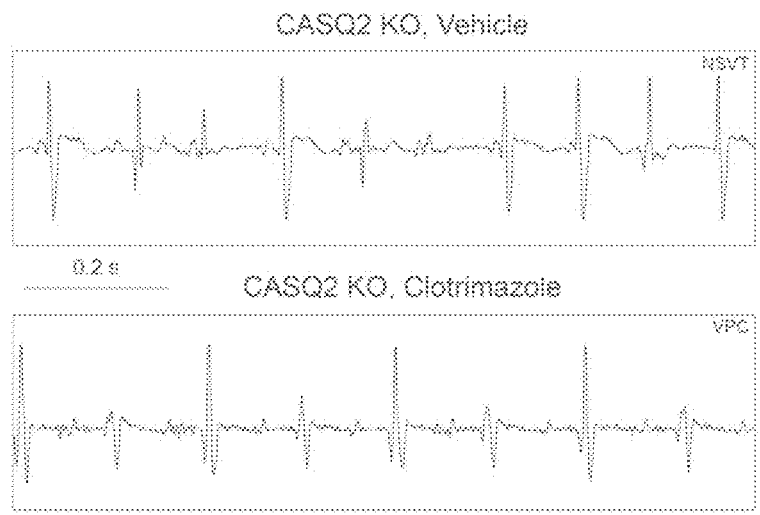
Figure 10D:
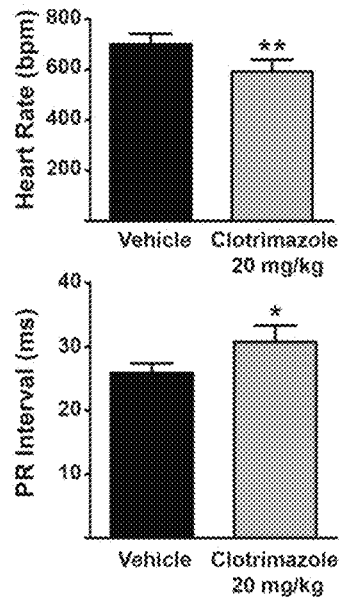

FIGS. 10A-D present representative ECG recording following IP injection of vehicle (FIG. 10A; upper) and 20 mg/kg clotrimazole (FIG. 10A; lower) in CASQ2-D307H KI mice during treadmill exercise; and corresponding data summary of heart rate (Paired t-test; **P=0.004, n=7) and PR interval (Paired t-test; *P=0.0305, n=7) in CASQ2-D307H KI mice during treadmill exercise (FIG. 10B); representative ECG recording following IP injection of vehicle (FIG. 10C; upper) and 20 mg/kg clotrimazole (FIG. 10C; lower) in CASQ2 KO mice during exercise; and corresponding data summary of heart rate (Paired t-test; **P=0.0037, n=7) and PR interval (Paired t-test; *P=0.0394, n=6) in CASQ2 KO mice during exercise (FIG. 10D).

FIG. 11 presents the chemical structures of exemplary SK4 blockers, taken from Wulff et al., Expert Rev Clin Pharmacol. 2010 May; 3(3): 385-396, which are usable in the context of some embodiments of the present invention.

DESCRIPTION OF SPECIFIC EMBODIMENTS OF THE INVENTION

The present invention, in some embodiments thereof, relates to therapy and, more particularly, but not exclusively, to methods of treating cardiac disorders, such as cardiac arrhythmia, and/or of inducing bradycardia, by blocking the $Ca^{2+}$-activated potassium channel SK4.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

$Ca^{2+}$-activated potassium channel SK4 (also referred to herein simply as SK4 channel) was previously identified in the pacemaker of immature cardiac cells (cardiomyocytes derived from human Embryonic stem cells) [Weisbrod et al., Proc Natl Acad Sci USA. 2013; FIGS. 1A-11)].

The present inventors have uncovered that SK4 channels are presented also in adult SAN cells and that blockers of SK4 channels reversibly reduce the pacing rate of isolated SAN cells. In vivo experiments in normal mice indicated that intraperitoneal injection of a SK4 blocker produces bradycardic effects, revealed in ECG recording by a significant increase in the PR interval. In addition, a prolongation of the PR interval revealed that SK4 $K^+$ channels also play a role in the heart conduction system.

SK4 channels were also identified in human induced pluripotent stem cell-derived cardiomyocytes (hiPS-CMs) from healthy and CPVT patients bearing a mutation in calsequestrin 2 (CASQ2-D307H) and in SAN cells from CASQ2-D307H knock-in (KI) mice. In vivo ECG recording showed that intraperitoneal injection of an SK4 channel blocker greatly reduced the ventricular arrhythmic features of CASQ2-D307H KI and CASQ2 knockout mice at rest and following exercise.

FIGS. 2A-C present data showing the existence of SK4 channel also in adult heart cells, and the pharmacological effects of clotrimazole on the pacemaker activity of adult SAN cells.

FIGS. 3A-D present data obtained in in vivo studies in mice, showing the effect of clotrimazole intraperitoneal injection on the mice heart rate following treadmill exercise and at rest.

FIGS. 4A-G present data showing the effect of TRAM-34 on the pacing rate of hiPS-CMs derived from CPVT2 patients.

FIGS. 5A-F and 6A-D present data showing the effect of TRAM-34 on SAN cells isolated from WT and CASQ2-D307H KI mice FIGS. 7A-F, 8A-F, 9A-D and 10A-D, and Table 1, present data obtained in in vivo studies in CASQ2-D307H KI and WT mice, showing the effect of TRAM-34 intraperitoneal injection on the heart rate and PR intervals at rest and during exercise.

The data presented herein demonstrate the pivotal role of SK4 $Ca^{2+}$-activated $K^+$ channels in adult pacemaker function, indicating that these channels are therapeutic targets for the treatment of cardiac ventricular arrhythmias such as CPVT and other cardiac and/or arrhythmia associated disorders.

The results presented herein clearly identify the $SK4/IK_{Ca}$ channel as a therapeutic target involved in the adult cardiac pacemaker mechanism.

The results presented herein show that the exemplary SK4 blockers clotrimazole and TRAM-34 exhibit a bradycardic effect, while elongating the PR interval and the refractory period between two heartbeats (effect in the Atrioventricular node manifested by an increase of the PR interval), like β1-adrenergic or $Ca^{2+}$ channel blockers. This effect was demonstrated at the cellular level in human and mice cardiac cells and also in vivo.

The data presented herein primarily provide the first evidence that SK4 channels are not only expressed in spontaneously beating hESC-CMs and hiPS-CMs but in adult SAN cells too. Inhibition of SK4 $K^+$ currents by TRAM-34 reduced the intrinsic SAN firing rate. These data reveal that in SAN cells SK4 channels are novel regulators of SAN automaticity.

The in vitro and in vivo data obtained with the SK4 channel blockers, TRAM-34 and clotrimazole, on the pacing rate of isolated SAN cells and on ECG parameters of WT mice, as presented herein, indicate that activation of SK4 channels increases the SAN pacing rate and their blockade reduces it. Both SK4 channel blockers produced significant bradycardic effects during rest and following treadmill exercise, without an indirect impact on autonomic input to SA and AV nodes.

The results presented herein further indicate that SK4 channels play a critical role in normal and CPVT diseased pacemaker function. These data indicate that SK4 channel blockers could be beneficially utilized in the management of CPVT patients' rhythm disorders.

The data presented herein show that inhibition of SK4 $K^+$ channels rescues in vitro the cardiac arrhythmias exhibited by hiPS-CMs derived from CPVT2 patients carrying the CASQ2 D307H mutation and by SAN cells isolated from CASQ2-D307H KI mice. Hence, TRAM-34 markedly reduced the occurrence of DADs and abnormal $Ca^{2+}$ transients detected following exposure to the β-adrenergic agonist isoproterenol. SK4 channel blockers can therefore protect from deleterious ventricular arrhythmic features revealed by ECG in CASQ2-D307H KI and CASQ2 KO mice at rest and after treadmill exercise.

Ventricular premature complexes, non-sustained and sustained ventricular tachycardia were significantly reduced following a single IP injection (20 mg/kg) of clotrimazole or TRAM-34. The SK4 channel blockers protected the CASQ2-D307H KI and CASQ2 KO mice from harmful polymorphic ventricular tachycardia without being pro-arrhythmic by themselves, since neither sinus arrest nor 2nd order AV block were recorded in the animals, including WT mice.

Despite the blockade of SK4 channels, the functional redundancy of $Ca^{2+}$-activated $K^+$ channels likely preserves the delicate balance of inward and outward currents necessary for normal pacemaking.

Due to their bradycardic effect and slowed AV conduction, SK4 channel blockers are beneficial for preventing ventricular tachycardia by prolonging the refractory period, similarly to β1-adrenergic or $Ca^{2+}$ channel blockers, yet without involving the "adrenergic escape" phenomenon.

The bradycardic effect and slowed atrioventricular node conduction exhibited by SK4 channel blockers can therefore be beneficially utilized for preventing ventricular tachycardia by prolonging the refractory period, as an alternative to the currently used β1-adrenergic and $Ca^{2+}$ channel blockers, as well as in treating other cardiac arrhythmias of different etiologies, non-arrhythmic cardiovascular disorders (cardiac diseases), ventricular tachyarrhythmias in CPVT and possibly in other arrhythmic pathologies of different etiologies such as the long QT syndrome.

Embodiments of the present invention therefore relate to methods employing blockers of a SK4 channel. Embodiments of the present invention also relate to methods of screening and identifying lead candidates usable in the methods described herein, by determining blockade of a SK4 channel by the tested compounds.

Hereinthroughout, the phrase "SK4 channel" and phrases used herein interchangeably therewith, describe the intermediate-conductance calcium-activated potassium channel $K_{Ca}3.1$, which is also referred to in the art as IK1 channel or SK4 channel.

SK4 Channel Blockers:

Herein, the terms "SK4 channel blocker", "blocker of SK4 channel", "an agent that blocks SK4 channel", and "an agent that inhibits or inactivates SK4 channel", and grammatical diversions thereof, are used interchangeably, and describe an agent that blocks the SK4 channel and thus inhibits its function as a channel of potassium ions (a channel that allows potassium ions to cross the cell membrane).

Inhibition and/or inactivation of SK4 channel, as used herein, can be manifested as reducing the function of the channel by at least 10%, preferably by at least 20%, or at least 30%, or at least 40%, or at least 50%, or at least 60%, or at least 70%, or at least 80%, or at least 90% and in some embodiments, by 05%, 96%, 97%, 98%, 99% or even 100%.

Reduction in the function of SK4 channel is manifested, for example, by a reduction in the electrical current produced by the channel as is further described hereinafter.

The term "SK4 channel" in the context of blockers is meant to include SK4 channels as described herein throughout and in the art.

Determining if a compound is a blocker of SK4 potassium channel can be performed using methods known in the art, some are described hereinafter in the context of the screening method. Other methods are readily recognized by those skilled in the art.

Typically, a blocker of SK4 channel is a competitive antagonist that binds to the channel and prevents it from being activated by calcium ions, or is an agent that reduces the concentration of calcium ions that bind to the channel.

Any agent that blocks an SK4 channel is contemplated according to the present embodiments. The agent can be a biomolecule (e.g., a protein, a peptide (such as toxin), a nucleic acid construct, etc.) or a small molecule, and is preferably a small molecule.

In some embodiments, a SK4 blocker is selective towards SK4 channel. In some embodiments, a SK4 blocker is capable of blocking other calcium ion-activated channel and/or or a potassium channel.

In some embodiments, a SK4 blocker binds to the inner pore of the SK4 channel. Alternatively, the SK4 blocker binds to other sites of the SK4 channel, for example, the calcium/calmodulin binding pocket, as well as other sites.

Representative examples of SK4 channel blockers include, but are not limited to, the following:

Clotrimazole (see also FIGS. 1C and 11):

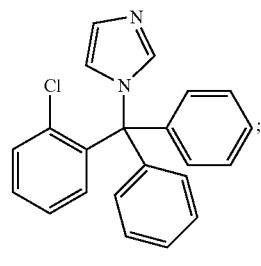

Clotrimazole

TRAM-34 (1-[(2-chlorophenyl)diphenylmethyl]-1H-pyrazole; a structural isomer of Clotrimazole; see, FIG. 11):

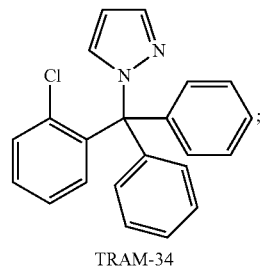

TRAM-34

ICA-17043 (4-fluoro-α-(4-fluorophenyl)-α-phenyl-benzeneacetamide; also known as Senicapoc®, see, FIG. 11):

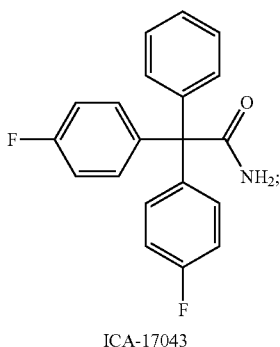 [SMILES: NC(=O)C(c1ccccc1)(c1ccc(F)cc1)c1ccc(F)cc1]

ICA-17043

Compounds (4)-(10) as depicted in FIG. 11;

Triarylmethans as described in WO 97/34589;

Fluorinated triphenyl acetamides as described in McNaughton-Smith et al., J Med Chem. 2008 Feb. 28; 51(4):976-82;

11-Phenyl-diazepines and Diphenylindanones such as described in U.S. Pat. Nos. 6,992,079 and 7,342,038;

4-Phenyl-4H-pyrans and related cyclohexasienes as described in Urbahns et al. Bioorg Med Chem Lett. 2003 Aug. 18; 13(16):2637-9; and Urbahns et al., Bioorg Med Chem Lett. 2005 Jan. 17; 15(2):401-4;

Cylcohexadiene lactones as described in DE-9619612645 1997;

The antimalarial agent quinine;

the vasodilator cetiedil;

the L-type Ca channel blockers nifedipine;

and nitrendipine.

Exemplary toxins which are known as SK4 blockers include, but are not limited to, the scorpion toxin charybdotoxin (ChTX); Maurotoxin (MTX); and the ChTX analog ChTX-Glu$^{32}$.

Any other blockers of SK4 channel as defined herein are also contemplated.

It is expected that during the life of a patent maturing from this application many relevant SK4 blockers will be developed and the scope of the term "blocker of SK4 channel" is intended to include all such new technologies a priori.

Therapeutic Applications:

According to an aspect of some embodiments of the present invention there is provided a method of inducing bradycardia (slowing a heart rate) in a subject in need thereof.

The term "bradycardia", which is also known as "bradyarrhythmia", as used herein and in the art, describes a slow heart rate in a subject compared to a normal, average, heart rate of a healthy subject of the same age and species, or compared to a heart rate associated with a subject's medical condition.

Bradychardia can be determined, for example, by electrocardiography (ECG).

The term "bradychardia" encompasses atrioventricular nodal bradycardia (AV junction rhythm), which usually appears on an ECG with a normal QRS complex accompanied with an inverted P wave either before, during, or after the QRS complex, and ventricular bradycardia, which is manifested by a slow heart rate (e.g., of less than 50 BPM in human adult), which usually appears as imbalanced relationship between P waves and QRS complexes in ECG. By "inducing bradycardia" are encompassed slowing a heart rate of a subject (e.g., reducing the heart rate of the subject by, for example, at least 5% or at least 10% or at least 20% or at least 30%, or at least 40% or at least 50%, compared to the heart rate of the same subject before treatment), and/or regulating an increased heart rate such that the heart rate of the subject is within the acceptable range of a healthy subject (e.g., of the same age and other parameters), and/or decreasing the sinus rate (by, for example, at least 5% or at least 10% or at least 20% or at least 30%, or at least 40% or at least 50%, compared to the sinus rate of the same subject before treatment) and/or elongating/prolonging the PR interval (by, for example, at least 5% or at least 10% or at least 20% or at least 30%, or at least 40% or at least 50%, compared to the PR interval of the same subject before treatment).

A "Sinus rate", which is also known and referred to in the art as "sinus rhythm", can be defined by the morphology of P waves in ECG.

"PR interval", which is also known and referred to in the art as "PQ interval" can be defined as the period that extends from the beginning of the P wave (the onset of atrial depolarization) until the beginning of the QRS complex (the onset of ventricular depolarization), in ECG.

According to some of any of the embodiments described herein, inducing bradycardia is effected by blocking a SK4 channel in the subject.

According to some of any of the embodiments described herein, inducing bradycardia is effected by blocking a SK4 channel in SAN cells of the subject.

According to an aspect of some embodiments of the present invention there is provided a method of treating a medical condition in which inducing bradycardia (slowing a heart rate) is desirable or beneficial in a subject in need thereof, the method comprising blocking a SK4 channel in SAN cells of the subject.

In some of any of the embodiments described herein, blocking the SK4 channel comprises administering to the subject an effective amount (e.g., a therapeutically effective amount) of a blocker of a SK4 channel, as defined herein in any of the respective embodiments.

In the context of these embodiments, an effective amount is an amount sufficient to reduce or inhibit a function of a SK4 channel, as defined herein.

According to an aspect of some embodiments of the present invention there is provided a method of reducing the firing of SAN cells, the method comprising contacting SAN cells with a blocker of SK4 channel.

In some embodiments, the contacting is effected in vitro, and the SAN cells are isolated from a subject as described herein.

In some embodiments, the contacting is effected in vivo, by administering to a subject in need of firing SAN cells, an effective amount (e.g., a therapeutically effective amount) of a blocker of SK4 channel as defined herein in any of the respective embodiments.

In the context of these embodiments, an effective amount is an amount sufficient to reduce or inhibit a function of a SK4 channel, as defined herein.

In some embodiments, the SAN cells are human SAN cells. In some embodiments, the SAN cells are of a human subject which is a post-natal subject (e.g., an adult subject).

According to an aspect of some embodiments of the present invention there is provided a method of inducing bradycardia (slowing a heart rate) in a subject in need thereof, the method comprising administering to the subject a blocker of a SK4 channel, as defined herein in any of the respective embodiments.

Subjects in need of induction of bradychardia include, for example, subjects suffering from a medical condition in which inducing bradycardia (slowing a heart rate) is desirable or beneficial, as described herein. According to an aspect of some embodiments of the present invention there is provided a method of treating a medical condition in which inducing bradycardia (slowing a heart rate) is desirable or beneficial in a subject in need thereof, the method comprising administering to the subject a blocker of a SK4 channel, as defined herein in any of the respective embodiments.

In some embodiments, the medical condition is a cardiac disease or disorder, and in some embodiments, the medical condition is a cardiac arrhythmia disease or disorder.

In some embodiments, the medical condition is associated with cardiac arrhythmia.

In some embodiments, the method according any of the respective embodiments can be used to treat cardiac disorders characterized by abnormal cardiac rhythm, such as, for example, cardiac arrhythmia.

In some embodiments, the medical condition is not directly associated with cardiac arrhythmia.

In some embodiments, the medical condition is such that requires a procedure which is advantageously performed while slowing a heart rate of the subject, for example, a surgery that involves interception of an organ or tissue of the cardiovascular system or any other operation of the cardiovascular system. An example is an open heart surgery.

In some embodiments, the medical condition is Myocardial Infarction (MI).

Any other cardiac as well as non-cardiac diseases or disorders or medical conditions in which slowing a heart rate is beneficial are contemplated.

According to an aspect of some embodiments of the present invention there is provided a method of treating cardiac arrhythmia or a medical condition associated with cardiac arrhythmia in a subject in need thereof, the method comprising administering to the subject a blocker of a SK4 channel, as defined herein in any of the respective embodiments.

As used herein the phrase "cardiac arrhythmia" refers to a variation from the normal rhythm of the heart rate, for example, tachycardia.

The cardiac arrhythmia can be a ventricular arrhythmia, an atrial arrhythmia, a juctional arrhythmia and a heart block.

Medical conditions associated with atrial arrhythmia include, but are not limited to, Premature atrial contractions (PACs), Wandering atrial pacemaker, Atrial tachycardia, Multifocal atrial tachycardia, Supraventricular tachycardia (SVT), Atrial flutter, and Atrial fibrillation (Afib).

Medical conditions associated with junctional arrhythmia include, but are not limited to, AV nodal reentrant tachycardia, Junctional rhythm, Junctional tachycardia, and Premature junctional contraction Medical conditions associated with ventricular arrhythmia include, but are not limited to, Premature ventricular contractions (PVCs), sometimes called ventricular extra beats (VEBs), Premature ventricular beats occurring after every normal beat are termed "ventricular bigeminy", Accelerated idioventricular rhythm, Monomorphic ventricular tachycardia, Polymorphic ventricular tachycardia, Ventricular fibrillation, and Torsades de pointes.

Medical conditions associated with heart block include, but are not limited to, AV heart blocks, which arise from pathology at the atrioventricular node, including First degree heart block, which manifests as PR prolongation, Second degree heart block, including Type 1 Second degree heart block, also known as Mobitz I or Wenckebach, and Type 2 Second degree heart block, also known as Mobitz II, and Third degree heart block, also known as complete heart block.

Exemplary medical conditions associated with cardiac arrhythmia include, but are not limited to, atrial fibrillation, ventricular fibrillation, conduction disorders, premature contraction, and tachycardia.

Conduction disorders collectively encompass abnormal or irregular progression of electrical pulses through the heart, which cause a change in the heart rhythm. Conductions disorders are not necessarily associated with arrhythmia but sometimes are the cause of arrhythmia. Exemplary conductions disorders include, but are not limited to, Bundle Branch Block, heart block, including first-, second- and third-degree heart block, and long Q-T syndrome.

Premature contraction includes premature atrial contractions and premature ventricular contractions.

Additional exemplary medical conditions associated with arrhythmia include Adams-Stokes Disease (also called Stokes-Adams or Morgangni), atrial flutter, which is usually found in patients with: Heart failure, Previous heart attack, Valve abnormalities or congenital defects, High blood pressure, Recent surgery, Thyroid dysfunction, Alcoholism (especially binge drinking), Chronic lung disease, Acute (serious) illness, Diabetes, after open-heart surgery (bypass surgery), or atrial fibrillation; Sick Sinus syndrome; sinus arrhythmia and Wolff-Parkinson-White (WPW) syndrome.

In some of any of the embodiments described herein, the cardiac disease or disorder is associated with tachycardia.

In some embodiment, a method as described herein is for treating or preventing tachycardia.

The term "tachychardia", which is also known as "tachyarrhythmia", as used herein and in the art, describes a fast heart rate in a subject compared to a normal, average, heart rate of a healthy subject of the same age and species, or compared to a heart rate associated with a subject's medical condition.

Tachychardia can be determined, for example, by electrocardiography (ECG), and encompasses a wide range of conditions, as listed herein throughout.

In some embodiments, the tachycardia encompasses atrial and Supraventricular tachycardia (SVT), including paroxysmal atrial tachycardia (PAT) or paroxysmal supraventricular tachycardia (PSVT); Sinus tachycardia, which can be associated with disorders of that heart which interfere with the normal conduction system of the heart, including, but not limited to, Lack of oxygen to areas of the heart due to lack of coronary artery blood flow, Cardiomyopathy in which the structure of the heart becomes distorted, Medications, Illicit drugs such as cocaine, and Sarcoidosis (an inflammatory disease affecting skin or other body tissues).

In some embodiments, the tachycardia is a ventricular tachycardia, a supraventricular tachycardia, atrial fibrillation, AV nodal reentrant tachycardia (AVNRT), or a AV reentrant tachycardia (AVRT).

In some embodiments, the cardiac disease or disorder is CPVT, as described herein and in the art.

In some embodiments, the cardiac disease or disorder is a long QT syndrome.

The subject to be treated according to some of any of the embodiments of the present invention can be a mammal, preferably a human being, including a baby, an infant, and an adult.

In some of any of the embodiments described herein, the subject is a post-natal subject.

In some embodiments, the subject is afflicted by, or suffers from, any of the medical conditions as described herein.

Tachycardia and bradycardia are defined in a subject in accordance with acceptable heart rates defined as normal in accordance with a subject's age.

According to an aspect of some embodiments of the present invention there is provided a blocker of SK4 channel for use in inducing bradycardia, or in treating any of the medical conditions described herein.

According to an aspect of some embodiments of the present invention there is provided a use of blocker of SK4 channel in the manufacture of medicament for use in inducing bradycardia, or in treating any of the medical conditions described herein.

In some of any of the embodiments described herein, the SK4 blocker can be used in combination with an additional active agent, for example, an agent usable in treating a medical condition as described herein.

In some embodiments the additional agent is a blocker of an SK channel. In some embodiments, the additional agent is an anti-arrhythmic agent (e.g., a beta blocker).

The SK4 blockers according to the present embodiments, optionally in combination with one or more additional active agent(s) as described herein, can be used (administered to a subject) per se or can form a part of a pharmaceutical composition that further comprises a carrier.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the SK4 blocker as described herein.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

In some embodiments, the agent is a fluid (e.g., liquid) carrier and in some embodiments, the SK4 blocker is dissolvable, dispersible or suspendable in the carrier.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

For buccal administration, the compositions may take the form of tablets or lozenges formulated in conventional manner.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Alternatively, the active ingredient may be in powder form for constitution with a suitable vehicle, e.g., sterile, pyrogen-free water based solution, before use.

The pharmaceutical composition of some embodiments of the invention may also be formulated in rectal compositions such as suppositories or retention enemas, using, e.g., conventional suppository bases such as cocoa butter or other glycerides.

Pharmaceutical compositions suitable for use in context of some embodiments of the invention include compositions wherein the active ingredients are contained in an amount effective to achieve the intended purpose. More specifically, a therapeutically effective amount means an amount of active ingredients effective to prevent, alleviate or ameliorate symptoms of a medical condition (e.g., as described herein) or prolong the survival of the subject being treated.

Determination of a therapeutically effective amount is well within the capability of those skilled in the art, especially in light of the detailed disclosure provided herein.

Compositions of some embodiments of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

A pharmaceutical composition as described herein can also include one or more additional active agents as described herein.

A pharmaceutical composition as described herein is also referred to as a medicament.

Screening Method:

According to an aspect of some embodiments of the present invention there is provided a method of identifying a candidate compound for treating an arrhythmic cardiac disorder (cardiac arrhythmia, as described herein in any of the respective embodiments). The method, according to these embodiments, comprises:

contacting a compound identified as a blocker of SK4 potassium channel with SAN cells; and determining if the compound reduces a pacing rate of said SAN cells, wherein a compound that reduces a pacing rate of said SAN cells is identified as a candidate compound for treating an arrhythmic cardiac disorder.

According to some embodiments, identifying a compound as a blocker of a SK4 potassium channel can be effected by:

contacting the compound with cells expressing SK4 potassium channel; and determining if a SK4 current amplitude is reduced upon said contacting, wherein a compound that causes a reduction in said SK4 current amplitude upon said contacting is identified as a blocker of a SK4 channel.

In some embodiments, the cells expressing SK4 potassium channels are transfected cells ectopically expressing a SK4 potassium channel (e.g., by means of cDNA encoding SK4 channel). Alternatively, cells inherently expressing SK4 potassium channels can be used.

In some embodiments, the contacting with cells expressing SK4 potassium channel is effected in vitro.

In some embodiments, determining if a SK4 current amplitude is reduced is effected by measuring the SK4 current amplitude, or preferably, a change in the SK4 current amplitude, upon contacting the compounds, compared with the SK4 current amplitude without contacting the compound.

In some embodiments, identifying a compound as a blocker of a SK4 channel is effected by screening a plurality of compounds, and determining their effect on the SK4 channel, for example, by measuring the SK4 current amplitude, or preferably, a change in the SK4 current amplitude, upon contacting the compounds, compared with the SK4 current amplitude without contacting the compound.

In some embodiments, compounds identified in this screening as SK4 channel blockers are tested for their effect on the pacemaking activity of SAN cells.

In some embodiments, a compound identified as a blocker of SK4 channel is known as such and its effect on SAN cells is determined without determining its blocking activity.

In some of any of the embodiments described herein, contacting the compound with the SAN cells is effected in vitro.

In some embodiments, the SAN cells are obtained from induced pluripotent stem cells-derived pacemaker cells and/or from a subject suffering from an arrhythmic cardiac disorder. The subject can be a human subject, or an animal subject, and can be a pre-natal or post-natal subject, preferably a post-natal subject.

In some embodiments, once a compound is identified as capable of reducing the pace rate of SAN cells, preferably in in vitro screening as described herein, it is determined as a candidate for treating a medical condition associated with arrhythmia, as described herein.

In some embodiments, the candidate compound is administered to a subject suffering from an arrhythmic disorder (e.g., cardiac arrhythmia as described herein) to thereby determine an effect of the compound on a heart rate of the subject.

In an exemplary screening method according to the present embodiments, a plurality of compounds are tested for their capability of exerting a blocking activity on SK4 channels expressed ectopically (heterologous expression) in transfected CHO cells.

The compounds identified as blockers of SK4 channels in transfected cells are then tested in vitro in SAN cells from iPS (induced pluripotent stem cells-derived pacemaker cells) from control (healthy) and from CPVT patients or patients afflicted by another arrhythmia disorder. Compounds which induce a bradycardia effect on control SAN iPS cells, and which rescue the arrhythmic features (notably DADs [delayed after depolarization]) in SAN cells from patients suffering from CPVT or another arrhythmia disorder, are identified as lead candidates for treating arrhythmia.

The term "treating" refers to inhibiting, preventing or arresting the development of a pathology (disease, disorder or condition) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology.

As used herein, the term "preventing" refers to keeping a disease, disorder or condition from occurring in a subject who may be at risk for the disease, but has not yet been diagnosed as having the disease.

As used herein, the term "subject" includes mammals, preferably human beings at any age which suffer from the pathology. Preferably, this term encompasses individuals who are at risk to develop the pathology.

It is expected that during the life of a patent maturing from this application many relevant methods for determining SK4 channel activity and/or SAN cells activity will be developed and the scope of these terms is intended to include all such new technologies a priori.

As used herein the term "about" refers to ±10% or ±5%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Materials and Methods

Animals:

SvEv mice β-6 months old) homozygous for the CASQ2 D307H mutation [CASQ2 D307H Knock-in (KI)] or for the off-frame exon 9 deletion [CASQ2Δ/Δ knock-out (KO)] and matched wild-type (WT) mice were used. Mice were maintained and bred in a pathogen-free facility on regular rodent chow with free access to water and 12-hour light and dark cycles. The procedures followed for experimentation and maintenance of the animals were approved by the Animal Research Ethics Committee of Tel Aviv University (M-14-063) in accordance with Israeli law and in accordance with the Guide for the Care and Use of Laboratory Animals (1996, National Academy of Sciences, Washington, D.C.).

Human Induced-Pluripotent Stem Cell Culture and Cardiac Differentiation:

Human induced pluripotent stem cells (hiPS) derived from normal healthy individuals and from patients bearing the CASQ2 D307H mutation (CPVT2) were grown on mitomycin C-inactivated mouse embryonic fibroblasts (MEF), in order to maintain them in an undifferentiated state. The cells were maintained pluripotent in a culture medium containing 80% DMEM F-12 (Biological Industries), 20% Knock Out SR (Invitrogen), 2 mM L-glutamine, 0.1 mM β-mercaptoethanol (Gibco), and 1% NEA (Gibco), supplemented with 4 ng/mL bFGF (Invitrogen). The medium was replaced daily until the colonies were ready to passage (every 4-5 days). For EBs induction (d0), hiPS colonies were removed from their MEF feeder by collagenase IV treatment and collected. After centrifugation, the cells were resuspended in EBs medium containing 80% DMEM (Gibco), 20% FBS (Biological Industries), 1% NEA, and 1 mM L-Glutamine and plated on 58-mm Petri dishes. After 7 d of culture in suspension, EBs were plated on 0.1% gelatin-coated plates and checked daily until a spontaneous beating activity was visible. Because CASQ2 is lately expressed in hiPS-CMs, 25 days-old EBs were used. The beating clusters were mechanically 279 dissected from EBs, following a three-step dissociation protocol. The hiPS-CMs were isolated and plated on Matrigel-coated glass coverslips (13 mm diameter) in 24-well plates. The coverslips were then incubated at 37° C., and a recovery period of 2 d was given before any electrophysiological experiment was performed.

Mouse SAN Dissection and Cell Dissociation:

WT and CASQ2 D307H KI mice were anesthetized with isofluorane and sacrificed by cervical dislocation. The heart was rapidly removed and transferred into Tyrode solution containing heparin. After the atria were pined and the superior and inferior vena cava localized, the ventricles were removed. The SAN was anatomically identified between the superior and inferior vena cava, the crista terminalis and the interatrial septum. The area was cleaned, cut into small strips and washed into a Low Calcium Solution, containing (in mM): 140 NaCl, 5.4 KCl, 0.5 $MgCl_2$, 1.2 $KH_2PO_4$, 5 HEPES-NaOH, 50 taurine, 5.5 glucose (pH 6.9). The osmolarity was adjusted if needed to 315 mOsm.

The same solution, supplemented with 1 mg/ml albumin, 200 μM $CaCl_2$, collagenase Type I (Worthington) or liberase TH (Roche), protease (Sigma) and elastase (Sigma) was used for enzymatic digestion as previously described [See, Mesirca, P., et al. *Nat Commun* 5, 4664 (2014)]. In this step, the tissue was gently resuspended with a polished Pasteur pipette in this solution for 9-13 minutes at 37° C. SAN samples were then washed three times in a modified "Kraftbrühe" solution, containing (in mM): 70 glutamic acid, 80 KOH, 20 KCl, 10 γ-Hydroxybutyric acid sodium salt, 10 $KH_2PO_4$, 10 HEPES-KOH, 10 taurine, 1 mg/ml albumin, 0.1 EGTA-KOH (pH 7.2). The same solution was used to re-suspend the single cells with a pipet by vigorous up and down, between 3 to 5 minutes at 37° C. Cells were then gradually exposed to increasing concentrations of calcium, following a "$Ca^{2+}$ readaptation" protocol [Mesirca et al., 2014, supra]. Experiments were performed the same day at 33° C.

Drugs:

Isoproterenol, clotrimazole and E-4031 were purchased from Sigma, while ZD-7288 and TRAM-34 from Tocris. For in-vivo telemetric recordings, Tram-34 was solubilized into peanut oil, while clotrimazole was prepared in peanut oil supplemented with 1% ethanol.

Electrophysiology:

In all experiments, the coverslips were perfused at 33° C. with an external solution containing (in mM): 140 NaCl, 4 KCl, 11 Glucose, 1.2 $MgCl_2$, 1.8 $CaCl_2$, 5.5 HEPES titrated to pH 7.4 with NaOH and adjusted at 320 mOsm with sucrose.

Whole-cell patch-clamp recordings were performed with an Axopatch 700B amplifier (Molecular Devices) and pCLAMP 10.5 software (Molecular Devices).

Signals were digitized at 5 kHz and filtered at 2 kHz using microelectrodes with resistances of 4-7 MΩ were pulled from borosilicate glass capillaries (Harvard Apparatus) and filled with an intracellular solution containing (in mM): 130 KCl, 5 MgATP, 5 EGTA, 10 HEPES titrated to pH 7.3 with KOH and adjusted at 290 mOsm with sucrose. Unless otherwise stated, internal free calcium concentrations were 100 nM and 1 μM for current-clamp and voltage-clamp experiments, respectively and were titrated with EGTA and $CaCl_2$ using the MaxChelator software.

The spontaneous automaticity of isolated SAN cells was recorded under perforated-patch conditions by adding 30 μM β-escin49 to the intracellular solution containing (in mM): 130 KCl, 10 NaCl, 10 HEPES, 0.2 EGTA-KOH, 2 MgATP, 6.6 Phosphocreatine, 0.05 cAMP and 1 μM free $Ca^{2+}$ (pH 7.2). To record SK4 K+ current, a voltage ramp protocol was applied. SAN and hiPS-CMs were held at −40 mV and −20 mV, respectively to substantially inactivate voltage-gated $Na^+$ and $Ca^{2+}$ currents. Cells were stepped from −90 mV to +60 mV for 150 ms. Then, a cocktail (solution 1) containing (in mM) 0.3 cadmium, 0.025 ZD-7288 and 0.01 E-4031 was applied extracellularly to inhibit residual L-type and T-type voltage-gated Ca2+ currents, $I_f$ and the IKr currents, respectively. Subsequently, TRAM-34 (5 μM) was added to solution 1 to inhibit SK4 $K^+$ currents, which were defined as TRAM-34 sensitive currents. For voltage-clamp recording of SAN cells, the intracellular solution was the same to that described above for recording spontaneous automaticity.

Calcium Transient Measurements:

SAN tissue preparations were dissected ex vivo from WT and CASQ2-D307H KI mice as described in Torrente, A. G., et al. *Proc Natl Acad Sci USA* 112, 9769-9774 (2015). The dissected whole SAN tissue was pinned on a hand-made chamber and was incubated in a Tyrode solution containing 10 μM Fluo-4 AM (Thermo Fisher Scientific) and pluronic acid for 1 hour at 37° C. in the dark. The SAN tissue was washed in Tyrode at 37° C. in the dark for 10 minutes before experiments. Fluorescence of calcium transients was recorded using a photomultiplier (PTi D-104) at 35° C. and the analog signals were digitized using Digidata 1440 (Molecular Devices) and analyzed with pCLAMP 10.5 software.

Western Blotting:

Mouse atrial and ventricular tissues cut in small pieces (left and right atrial appendages, left and right ventricles, sinoatrial node) or beating clusters from normal and CASQ2-D307H hiPS-CMs were resuspended in ice-cold lysis buffer [50 mM Tris-HCl pH 7.5, 100 mM NaCl, 1% Nonidet P-40, 0.1% SDS, supplemented with protease cocktail inhibitor (Sigma-Aldrich) and 1 mM phenylmethylsulfonyl fluoride (Sigma-Aldrich)], incubated on ice for 45 minutes, shaken by vortex every 2-3 minutes and centrifuged for 15 minutes at 4° C. at 16,000×g. Equal amounts of proteins (30 μg) of the resulting lysate supernatant were mixed with Laemmli sample buffer and fractionated by 10% SDS/PAGE. The resolved proteins were electro-blotted onto a nitrocellulose membrane. The membrane was incubated with the primary antibodies followed by horseradish peroxidase-conjugated secondary anti-IgG antibodies (1:10, 000). The primary antibodies were diluted into 5% skim milk-TBST ((Tris-buffered saline, 0.1% TWEEN® 20). The mouse anti-SK4/KCa3.1 (SAB1409264 Sigma 1:1000) was used for rodent lysates and the rabbit anti-SK4/KCa3.1 (AV35098 Sigma 1:2500) was used for human hIPS18 CMs lysates. Both SK4 antibodies were 347 incubated overnight at 4° C. The rabbit anti-Casq2 (18422-1-AP proteintech, 1:2500) and the mouse monoclonal anti β-actin (MP Biomedical clone C4 691001 1:10,000) were incubated 1 hour at room temperature. Signals were developed using SuperSignal West Pico Chemiluminescent Substrate (Thermo Scientific).

In Vivo Telemetric Recordings:

Telemetric ambulatory long-term ECG recordings, analogous to Holter monitoring in humans, were obtained with implantable transmitters. WT, CASQ2-D307H KI and CASQ2 KO SvEv mice were anesthetized with ketamine (75-90 mg/kg) and xylazine (5-8 mg/kg) intraperitoneally (IP) (Kepro, Holland), and a midline incision was made along the spine. An implantable 3.5 grams wireless radiofrequency transmitter (DSI MM USA, device weight 3.8 grams) was aseptically inserted into a subcutaneous tissue pocket in the back as described in Katz, G., et al. *Heart Rhythm* 7, 1676-1682 (2010) and Kurtzwald-Josefson, E., et al. *Heart Rhythm* 11, 1471-1479 (2014)]. Animals were allowed to recover after surgery for at least 24 hours before any experiments. Baseline electrocardiograms (ECG) were obtained 15 minutes after IP injection of the appropriate vehicle (peanut oil or peanut oil supplemented with ethanol 1%). For pharmacological experiments, the same mouse was used a few hours after baseline ECG recordings (vehicle injection) and for subsequent ECG recordings upon IP injection of 20 mg/kg clotrimazole or TRAM-34. Telemetered ECG tracings were obtained in conscious mice at rest for one minute and during peak exercise (i.e. the first minute of recovery). In the treadmill exercise, mice were forced to exercise on a rodent treadmill; gradually increasing the speed up to a maximum of 15 m/minute. Ventricular tachycardia (VT) was defined as four or more consecutive ventricular beats. If this phenotype was consecutively observed for more than 15 seconds, it was defined as "sustained" ventricular tachycardia (SVT). Shorter VTs were characterized as "non-sustained" (NSVT). All other ventricular arrhythmias, such as premature beats, ventricular bigeminy, couplets and triplets were all defined as ventricular premature contractions (VPCs).

Data Analysis:

Rate, AP duration at 50% of repolarization (APD50), delayed afterdepolarizations (DADs), current densities and calcium transients were analyzed with the Clampfit program (pClamp 10.5; Molecular Devices). Leak subtraction was performed offline using the Clampfit software. Sinus rhythm, PR interval, and ECG arrhythmic features were analyzed with the LabChart 8 Reader (ADInstruments).

Data were analyzed with Excel (Microsoft) and Prism 5.0 (GraphPad Software) and are expressed as mean±SEM. Statistical analysis was performed using the two-tailed paired Student t test and the linear regression for correlation or by one way ANOVA followed by Tukey's Multiple Comparison Test. P values of less than 0.05 were assumed significant.

Example 1

SK4/$IK_{Ca}$ Channels as a Therapeutic Target in the Management of Cardiac Diseases Weisbrod et al. (2013, supra) studied the cardiac pacemaker process in human embryonic stem cells-derived cardiomyocytes (hESC-CMs), a cellular model which mimics the cardiac cells of the primitive heart during development. The currents involved in the pacemaker mechanism in these cells were investigated and, using biochemistry, electrophysiological and pharmacological techniques, the intermediate $Ca^{2+}$-activated potassium channel ($IK_{Ca}$/SK4, KCa3.1) was identified as a new target in the heart pacemaker mechanism.

The data obtained in these studies is presented in FIGS. 1A-D (Background Art). FIG. 1A presents data obtained in biochemical experiments revealing the existence of the SK4 protein on cardiomyocytes. Upper panel presents a Western blot from young and older hESC-CMs lysates showing a 50 KDa band corresponding to the SK4 channel. Lower panel presents immunocytochemistry showing the expression of SK4 in green and the cardiac marker α-actinin in red in the same single hESC-CMs. FIG. 1B presents electrophysiological characterization of the SK4 current in a single cardiac hESC-CM. Following a voltage-ramp protocol (electric stimulation from −90 to +40 mV), the whole conductances from the cell were recorded (black trace). Then, a solution 1 containing several pharmacological blockers was applied in order to neutralize the dominant cardiac currents. As a consequence, the amplitudes of the currents were decreased until linearization as shown on the green trace (solution 1 contained 10 µM zatebradine, 1 µM nifedipine and 10 µM E-4031, which are HCN blocker, $Ca^{2+}$ channel blocker and $IK_r$ blocker, respectively). Adding 2 µM of the SK4 blocker clotrimazole to the same solution 1 decreased the linear voltage trace in both sides (inward and outward, violet trace), confirming the existence of a "clotrimazole-sensitive"/SK4 current in those pacemaker cells. The chemical structure of clotrimazole is presented in FIG. 1C. FIG. 1D presents the pharmacological effects of clotrimazole on the cardiac pacing. The spontaneous electric activity of the cell was recorded in the current clamp configuration of the patch clamp technique before (black trace) and during exposure to 2 µM clotrimazole (violet trace). Clotrimazole decreased the firing rate of the cells, depolarized the membrane of the cell (MDP) until a pacing arrest. It did not significantly affect the duration of the action potentials ($APD_{50}$). Thus, exposing the cells to 2 µM clotrimazole in the external solution, dramatically decreases the rate of the spontaneous electrical pulses (action potentials) of the cardiac cells, culminating by a depolarization of the maximal depolarization potential (MDP) and arrest of the pacing. The absence of elongation of the action potential (no changes in the action potential duration "$APD_{50}$") discards the possibility of a role of the SK4 current in the repolarization (phase 3) of the action potential.

Because hESC-CMs display immature phenotypes, it was required to confirm the observations in adult heart cells. To this end, mice heart samples and human heart biopsia from patients were used. The obtained data is presented in FIGS. 2A-C. FIGS. 2A and 2B present biochemical experiments revealing the existence of the SK4 channel on murine heart (FIG. 2A) and in human right atrium and ventricle biopsia (FIG. 2B). In FIG. 2A, left panel presents a reverse transcriptase PCR of the SK4 mRNA showing a 286 bp band corresponding to the amplification of the channel transcript in different heart regions (SAN=sinoatrial node; RA=right appendage; LA=left appendage; RV=right ventricle, LV=left ventricle); and right panel presents Western blot on murine lysates from the same heart areas, showing a specific 50 KDa band corresponding to the SK4 channel. Thus, similarly to the observations in hESC-CMs, biochemical experiments performed in the right and left appendages, the right and left ventricles and the sinoatrial node isolated from mice showed a very clear expression of SK4 in those areas of the heart at the transcript and protein level.

In FIG. 2B it is shown that while the SK4 channel is observed at the transcript level in the right atrium and ventricle of several patients (left panel), it is only expressed at the protein level in the right atrium. Those results were confirmed in more than 64 right atrium biopsia from different patients (right panel). These data points towards the right atrium being the anatomical region of the heart that includes the SAN.

Cells from the mice SAN were successfully isolated, and electophysiological experiments were performed on their spontaneous pacing rate before and after applying clotrimazole. FIG. 2C presents the pharmacological effects of clotrimazole on the pacemaker activity of SAN cells. The spontaneous electric activity of the cell was recorded in the current clamp configuration of the patch clamp technique before (black trace) and during (violet trace) exposure to 2 µM clotrimazole. Clotrimazole strongly decreases the firing rate of the cells, leading to a bradycardic effect, which is reversible during washout (blue trace). These data show that clotrimazole led to a strong reduction of the pacing rate of the cells, pointing towards the importance of the SK4 channel in the pacemaker physiological mechanism. Importantly, it is shown that these effects are reversible when the cells are washed.

Example 2

Clotrimazole Induces Bradycardia

In order to demonstrate the importance of SK4 as a new therapeutic target in adult heart, the actions of clotrimazole were evaluated in vivo. For this, a heart telemetry device was implanted in norma mice for continuous ECG recording at rest and during treadmill exercise. For each session, continuous ECG recording was performed with the same animals receiving first intraperitoneal (IP) injection of vehicle (peanut oil) and then 20 mg/kg clotrimazole. The obtained data is presented in FIGS. 3A-D.

FIG. 3A presents representative ECG recording following intraperitoneal injection of vehicle (upper) and 20 mg/kg clotrimazole (lower) in norma mice at rest. Sequential vehicle and clotrimazole injections were performed on the same animal. Clotrimazole produced bradycardia (PP) and prolongation of the PR interval (grey arrows). FIG. 3B presents data summary of heart rate at rest (upper; *P=0.0364, n=10) and PR interval (lower; *P=0.0437, n=10).

FIG. 3C presents representative ECG recording following intraperitoneal injection of vehicle (upper) and 20 mg/kg clotrimazole (lower) in mice following treadmill exercise. Similarly to what happened at rest, clotrimazole produced a negative chronotropic effect (PP elongation). Despite the visible similar trend on the PR interval prolongation, the clotrimazole effect did not reach significance following treadmill exercise (n=10). FIG. 3D presents data summary of heart rate (upper; *P=0.0229, n=10) and PR interval (lower), which was 29.27±0.94 ms vs Clotrimazole 37.44±4.03 ms.

As shown in FIGS. 3A-B, a single injection of clotrimazole (20 mg/kg, IP) reduced the resting heart rate by 16.1±6.1% (from 718±16 bpm to 604±43 bpm, *P=0.0364, n=10) and prolonged the PR interval as it can be seen with the grey arrows (from 29.4±0.9 ms to 37.0±3.5 ms, *P=0.0437, n=10). These results confirm the importance of the SK4 channels not only in the SAN, but also in the whole cardiac conduction system. As shown in FIGS. 3C-D, a similar trend was observed during treadmill exercise. Injection of clotrimazole produced a similar reduction of the sinus rate, from 724±18 bpm to 605±42 bpm (*P=0.0229, n=10).

These results indicate that SK4 blockade by clotrimazole leads to sinus bradycardia and to an elongation of the refractoric period in normal mice and that clotrimazole can be used as an alternative to β-blocker or $Ca^{2+}$ channels blockers therapies to reduce the heart rate.

Example 3

SK4 Blockade for Treating CPVT

Decreasing the heartbeat with bradychardic medications such as β-blockers is a common and widely accepted therapeutic approach used in order to reduce the incidence of arrhythmia in several cardiopathies. By reducing the heartbeats, those compounds extend the refractory period between two contractions, thus decreasing the risks of arrhythmia.

Catecholaminergic polymorphic ventricular tachycardia (CPVT) is an inherited arrhythmogenic syndrome characterized by physical or emotional stress-induced polymorphic ventricular tachycardia in otherwise structurally normal hearts with a high fatal event rate in untreated patients. In a cellular level, ventricular cells but also SAN cells and other conductive pacemaker cells display abnormal cytoplasmic $Ca^{2+}$ levels. During exercise or stress (activation of the sympathetic system), those calcium events generate small and local depolarizations called "delayed afterdepolarizations" (DADs), which trigger an uncoupling between the normal sinoatrial rhythm and the ventricular activity. The consequence is the observation of a "ventricular tachycardia" (absence of P waves before the QRS complexes) observable during ECG recordings, which lead to cardiac arrest and sudden death if the patients are not treated or implanted with an implantable cardioverter defibrillator.

Studies were conducted in order to explore whether SK4 channels are expressed in SAN and play a role in CPVT.

Clotrimazole and TRAM-34 (an isomer of clotrimazole as depicted hereinabove) were tested on a model of ventricular disorder in order to see if SK4 blockade decreases the arrhythmic features.

Single spontaneously beating hiPS-CMs (25 days-old EBs) derived from normal (healthy) and CPVT2 patients carrying the CASQ2 D307H mutation were used and investigated for their spontaneous firing and ionic currents. A voltage ramp was applied as previously described [Wiesbrod et al., 2013, supra] and cells were held at −20 mV to substantially inactivate voltage-gated $Na^+$ and $Ca^{2+}$ currents. The data obtained in these studies is presented in FIGS. 4A-G.

FIGS. 4A-B presents representative traces of hiPS-CMs derived from normal (FIG. 4A) or CPVT2 (CASQ2 D307H) (FIG. 4B) patients. Cells were held at −20 mV and a voltage ramp of 150 ms from −90 to +60 mV was applied, as shown in FIG. 2B. The black traces show the various currents recorded with 1 μM internal free $Ca^{2+}$ and without blockers in the extracellular solution. The orange traces indicate that exposing cells to blocker solution 1 (300 μM $CdCl_2$, 25 μM ZD7288, and 10 μM E-4031), markedly depressed the inward humps and the currents in the inward and outward directions. The green traces reflect the addition of the selective SK4 channel blocker TRAM-34 (5 μM) to solution 1. The blue traces show the currents obtained when the cell was washed out with solution 1 alone.

As shown in FIGS. 4A-B, in the absence of blockers (black traces), the voltage ramp revealed the presence of two inward humps peaking at about −40 mV and −5 mV and reflecting activation of residual T type and L-type Ca2+ currents, respectively. These inward humps disappeared following exposure to 300 μM $CdCl_2$. Exposing cells to Solution 1 (300 μM CdCl2, 25 μM ZD7288, and 10 μM E-4031), suppressed the inward humps and markedly depressed inward and outward currents (orange trace). Addition of the selective SK4 channel blocker TRAM-34 (5 μM) to solution 1 reversibly (blue trace) decreased the currents in both inward and outward directions (green trace). This TRAM-34-sensitive current was never detected in zero internal free $Ca^{2+}$.

The TRAM-sensitive current was calculated as a difference between the current density measured at +60 mV with solution 1 alone (orange trace) and solution 1+5 μM TRAM-34 (green trace) (n=7-9), and is shown in FIG. 4C. Following TRAM-34 exposure, residual inward and outward currents could still be detected and likely correspond to non-selective cationic conductances, which shifted the reversal potential away from EK. TRAM-34 sensitive currents were observed in 7 out of 15 normal hiPS-CMs and in 9 out of 13 CPVT2 hiPSC-CMs. No significant differences were found in TRAM-34-sensitive current densities of normal and CPVT2 hiPSC-CMs.

FIG. 4D presents representative Western blots of beating EBs lysates from normal and CPVT2 (CASQ2 D307H) patients showing immuno-reactive SK4 protein (about 50 KDa). SK4 channel expression was thus confirmed at the protein level, where an SK4 immunoreactive band of about 50 kDa was identified in Western blots from beating cluster lysates of normal and CPVT2 hiPSC-CMs.

FIG. 4E (Left) presents representative traces of spontaneous APs recorded in hiPS-CM derived from a normal individual. Baseline pacing (control, black trace) was significantly increased following exposure of normal hiPSC532 CMs to 3 µM isoproterenol (red trace). Adding 5 µM TRAM-34 (green trace) depolarized the MDP and decreased the DD slope, which eventually culminated by a suppression of the pacing. The TRAM-34 effect was reversible by washout (blue trace). FIG. 4E (Right) are bar graphs presenting data summary of pacing rate (normalized to Ctrl; one-way ANOVA P=0.0071, n=14), DD slope (paired t-test, *P<0.0001, n=14) and APD50 (one-way ANOVA *P=0.0243, n=18). These data show that exposure of normal hiPSC-CMs to 3 µM isoproterenol significantly increased their firing rate and reduced their APD50. Adding 5 µM TRAM-34 depolarized the maximal diastolic potential (MDP), and significantly decreased the slope of diastolic depolarization (DD), which eventually culminated by a suppression of the pacing (in 10 out of 14 cells).

Figure 4F:
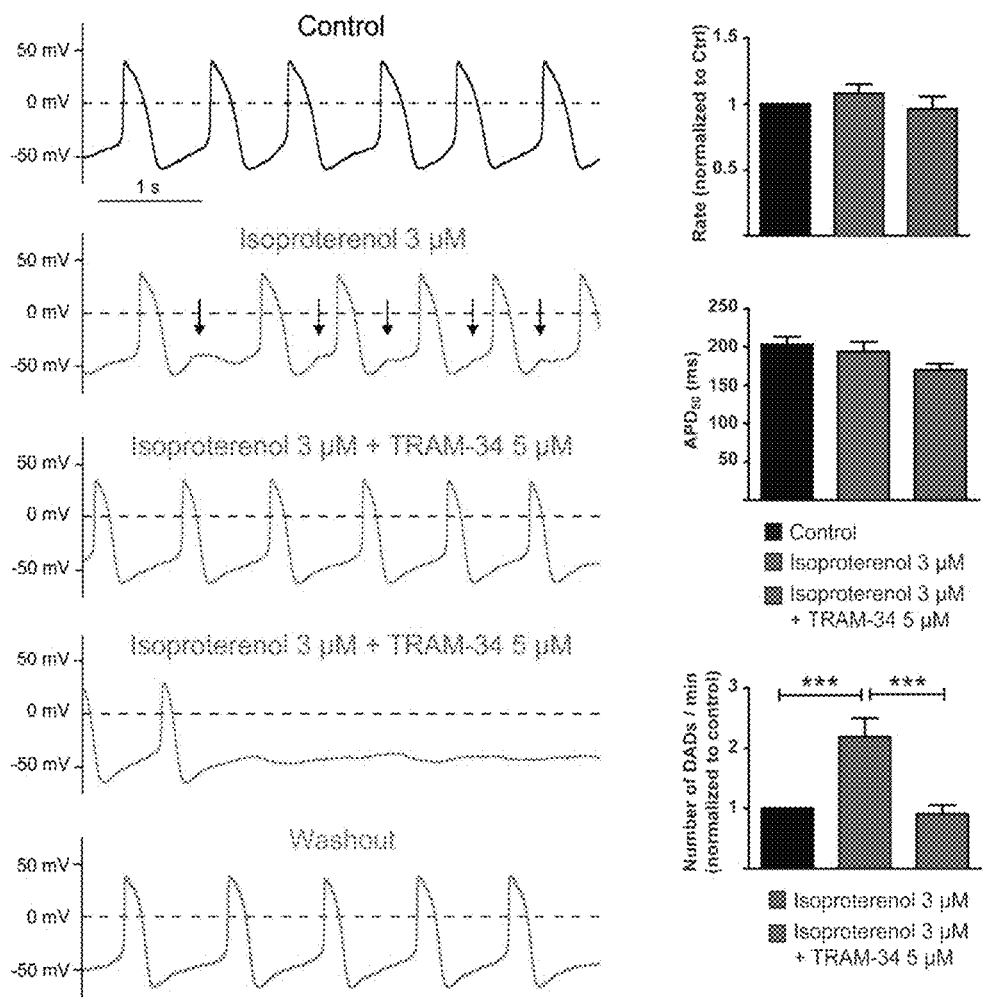

Similar experiments were performed on CASQ2 D307H hiPS-CMs and the obtained data is shown in FIG. 4F.

FIG. 4F (Left) presents representative traces of spontaneous APs recorded in hiPS-CM derived from a CPVT2 (CASQ2 D307H) patients. From a regular pacing (black trace), DADs appeared when the cell was exposed to 3 µM isoproterenol (red trace, arrows). Adding 5 µM TRAM-34 to isoproterenol markedly reduced the DADs (upper green trace) until the SK4 blockade led to the pacing arrest (lower green trace). The suppression of cell 540 automaticity was reversible upon washout (blue trace). FIG. 4F (Right) present bar graphs showing data summary of pacing rate (n=17), on APD50 (n=17) and DADs (Normalized to Ctrl; one-way ANOVA***P=0.0001, n=15).

These data show that Isoproterenol did not produce positive chronotropic effect on CPVT2 hiPSC-CMs. Instead, isoproterenol triggered DADs (see, FIG. 4F, arrows). Adding TRAM-34 to the isoproterenol solution drastically reduced the number of DADs and led to subsequent and reversible cessation of the spontaneous activity.

For selectivity purposes, it was examined whether TRAM-34 interfered with major pacemaker currents in hESC-CMs. It has been previously showed that If and INCX currents were unaffected by 5 µM TRAM-34 [Weisbrod et al., 2013, supra].

Figure 4G:
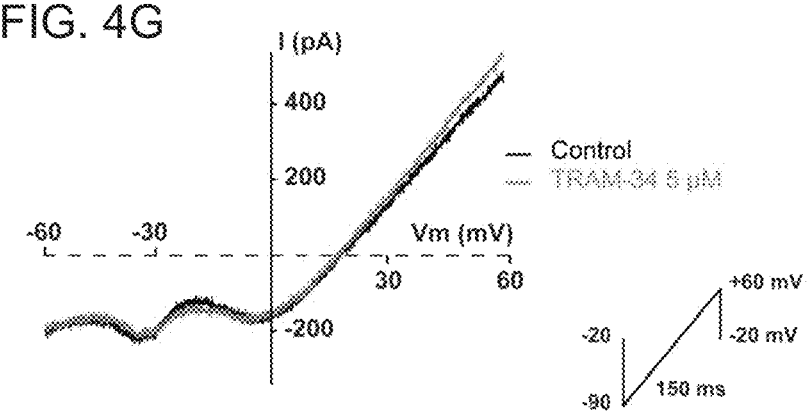

FIG. 4G presents representative trace of a voltage-ramp protocol performed in cardiomyocytes derived from human embryonic stem cells before (black trace) and after applying 5 µM TRAM-34 (red trace). Cells were held at −20 mV and a voltage ramp of 150 ms from −90 to +60 mV was applied. The experiments were performed in zero free Ca2+ in the pipet solution. In the absence of TRAM-34 (black traces), the voltage ramp revealed the presence of two inward humps peaking at about −40 mV and −5 mV and reflecting the activation of residual T type and L-type Ca2+ currents, respectively. Results show that 5 µM TRAM-34 (red trace) does not alter the voltage-gated Ca2+ currents (n=7). Thus, it was shown that 5 µM 90 TRAM-34 did not alter the T type and L type Ca2+ currents measured by the two inward humps (see, zero free $Ca^{2+}$ in pipet solution in FIG. 4G).

Example 4

Studies in SAN Cells from CASQ2-D307H KI Mice

Individual SAN cells were isolated from WT and CASQ2-D307H homozygous KI mice and recorded as described above, except that cells were held at −40 mV to improve their stability.

FIGS. 5A-B presents representative traces of SAN cells isolated from WT and CASQ2-D307H KI mice. Cells were held at −40 mV and a voltage ramp of 150 ms from −90 to +60 mV was applied. The black traces show the various currents recorded with 1 µM internal free $Ca^{2+}$ and without blockers in the extracellular solution. The orange traces indicate that cells were exposed to blocker solution 1. The green traces reflect the addition of TRAM-34 (5 µM) to solution 1. In the absence of blockers (black traces), the voltage ramp revealed the presence of only one inward hump peaking at about −40 mV and reflecting activation of T type $Ca^{2+}$ currents with minor contribution of L108 type $Ca^{2+}$ currents. The inward hump and substantial inward and outward currents disappeared upon exposure of cells to solution 1 (orange traces).

In FIG. 5C, the TRAM-sensitive current was calculated as in FIG. 4C (n=8-12). TRAM-34-sensitive currents with similar densities were isolated in SAN cells from both WT and CASQ2-D307H KI mice (green traces).

FIG. 5D presents representative Western blots of SAN lysates from WT and CASQ2-D307H KI mice showing the immuno-reactive bands of SK4, CASQ2 and β-actin proteins in SAN, right and left atrial appendages, right and left ventricle. The expression of SK4 channels and CASQ2 in adult mouse heart of WT and CASQ2-D307H KI mice was confirmed. Western blots of lysates from SAN, right and left atrial appendages, right and left ventricles showed specific immunoreactive bands corresponding to SK4 channel and to CASQ2 protein.

FIG. 5E (Left) presents representative traces of spontaneous APs recorded in single SAN cell from WT mice. Baseline pacing (control, black trace) was increased following exposure to 50 nM isoproterenol (red trace). Adding 2 µM TRAM-34 (green trace) depolarized the MDP and decreased the DD slope and eventually suppressed the pacing. FIG. 5E (Right) presents bar graphs showing data summary of pacing rate (paired t-test *P<0.049; n=4), DD slope (one-way ANOVA, ***P=0.0087, n=7) and APD50 (n=7). Isoproterenol (50 nM) significantly increased the pacing of SAN cells from WT mice with an increased DD slope. Adding 2 µM TRAM-34 to isoproterenol, depolarized the MDP, markedly reduced the DD slope, decreased the beating rate and eventually stopped the pacing activity in 3 out of 7 cells.

Figure 5F:
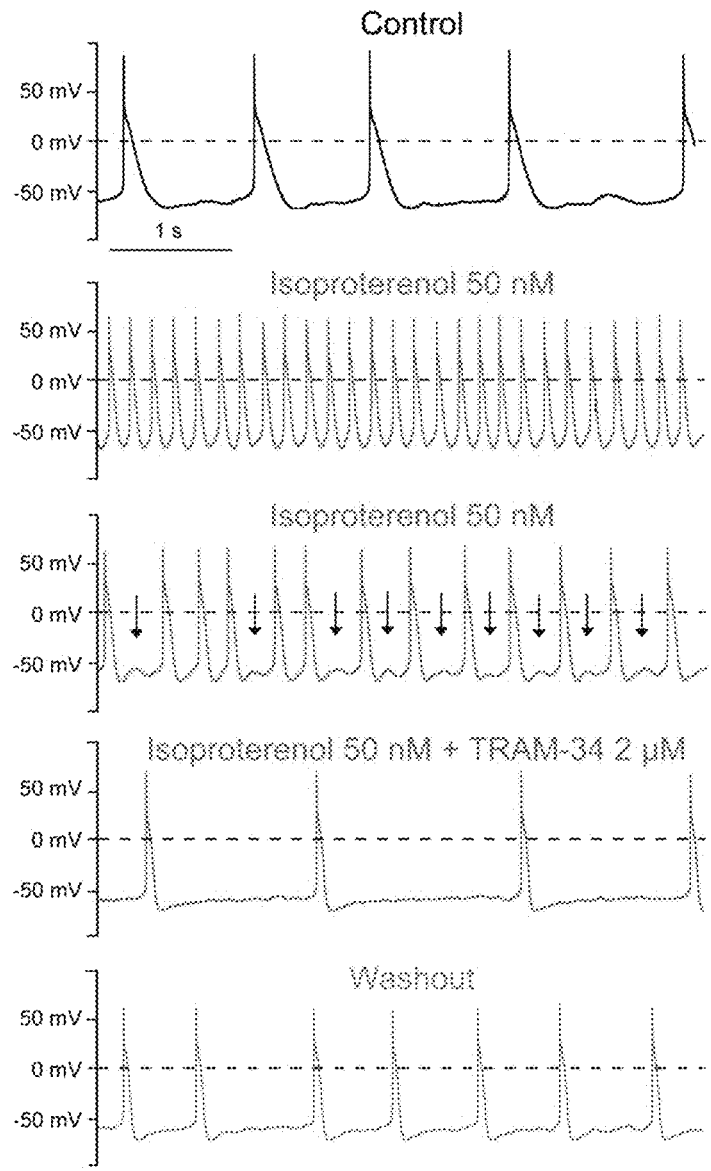
Figure 5F:
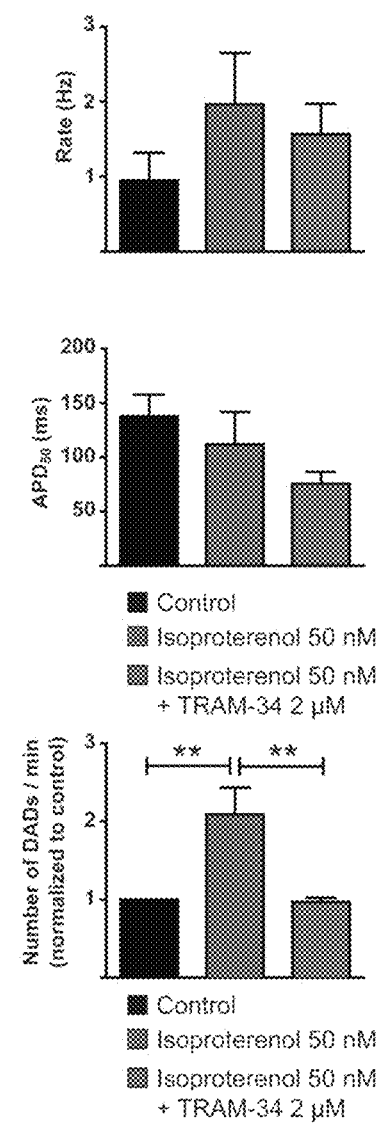

FIG. 5F (Left) presents representative traces of spontaneous APs recorded in single SAN cell from CASQ2 D307H KI mice. From a regular pacing (black trace), the rate increased and DADs appeared following addition of 50 nM isoproterenol (red trace, arrows). Adding 2 µM TRAM-34 to isoproterenol noticeably reduced DADs occurrence (green trace). FIG. 5F (Right) presents bar graphs showing data summary of rate (n=6), APD50 (n=6) and DADs (Normalized to Ctrl: one-way ANOVA,**P=0.0025, n=5).

In SAN cells from CASQ2-D307H KI mice, addition of 50 nM isoproterenol initially produced a positive chronotropic effect. However, after 1-2 minutes isoproterenol led to DADs (FIG. 5F, arrows). When 2 µM TRAM-34 were added to the isoproterenol solution the occurrence of DADs was drastically reduced.

To investigate the spontaneous calcium transients of the SAN, intact SAN tissue preparations dissected ex vivo from WT and CASQ2-D307H KI mice were exposed to Fluo-4 AM as previously described [Torrente, A. G., et al. *Proc Natl Acad Sci USA* 112, 9769-9774 (2015)].

FIG. 6A (Left) presents representative traces of spontaneous calcium transients recorded ex vivo in intact SAN tissue preparations from WT mice. The baseline rate of calcium transients (control, black trace) was significantly increased in presence of 100 nM isoproterenol (red trace) and the additional exposure of 2 μM TRAM-34 (green trace) did not alter the pattern of the $Ca^{2+}$ waves. Right: data summary of calcium transient rate (one-way-ANOVA***P=0.0003; n=12).

In SAN from WT mice, the rate of calcium transients was significantly increased in presence of 100 nM isoproterenol and the additional exposure of 2 μM TRAM-34 did not alter the pattern of the $Ca^{2+}$ waves.

Consistent with previous studies in different CPVT1 and CPVT2 mouse models and hiPSC-CMs, exposing SANs from CASQ2-D307H KI mice to 100 nM isoproterenol produced various $Ca^{2+}$ transient abnormalities, which were classified according to their degree of severity.

FIG. 6B presents representative traces of different types of calcium transient abnormalities recorded in intact SAN from CASQ2 D307H KI mice, termed as "local $Ca^{2+}$ release" (upper left), "double humped transients" (upper right), "large-stored released $Ca^{2+}$ waves" (lower left) and "calcium alternans" (lower right).

FIG. 6C presents representative trace of spontaneous calcium transients recorded from intact SAN of CASQ2 D307H KI. The baseline rate of calcium transients (control, black trace) yielded chaotic calcium transients (red trace) following incubation of the SAN with 100 nM isoproterenol. Subsequent addition of 2 μM TRAM-34 to the solution drastically improved the arrhythmic features of the calcium transients (green trace). FIG. 6D presents data summary of the arrhythmic calcium transients in SAN from CASQ2 D307H KI under baseline conditions, following exposure to 100 nM isoproterenol and 100 nM isoproterenol+2 μM TRAM-34.

Adding 2 μM TRAM-34 normalized the shapes of isoproterenol induced aberrant calcium waves in SAN from CASQ2-D307H KI mice. For instance, TRAM-34 brought back to zero the number of SANs displaying double humped transients or large-stored released $Ca^{2+}$ waves.

Example 5

In Vivo Studies

A heart telemetry device was implanted in WT, CASQ2-D307H KI and CASQ2 KO mice for continuous ECG recording at rest and during treadmill exercise. For each session, continuous ECG recording was performed with the same animals receiving first intraperitoneal (IP) injection of vehicle (peanut oil) and then the SK4 channel blocker. The obtained data is presented in FIGS. 7A-10D.

FIG. 7A presents Representative ECG recording following intraperitoneal injection of vehicle (upper) and 20 mg/kg TRAM-34 (lower) in WT mice at rest. Sequential vehicle and TRAM-34 injections were performed on the same animal. TRAM-34 produced bradycardia (PP) and prolongation of the PR interval (grey arrows). FIG. 7B presents data summary of heart rate (Paired t-test; *P=0.0003, n=10) and PR interval (Paired t test; *P=0.0004, n=10) in WT mice at rest.

FIG. 7C presents representative ECG recording following IP injection of vehicle (upper) and 20 mg/kg TRAM-34 (lower) in CASQ2-D307H KI mice at rest. TRAM-34 produced bradycardia and markedly reduced arrhythmic features such as ventricular premature complexes. FIG. 7D presents data summary of heart rate (Paired t-test; *P<0.0001, n=12) and PR interval (Paired t-test; *P=<0.0001, n=12) in CASQ2-D307H KI mice at rest.

FIG. 7E presents representative ECG recording following IP injection of vehicle (upper) and 20 mg/kg TRAM-34 (lower) in CASQ2 KO mice at rest showing that TRAM-34 produced similar effects as in CASQ2-D307H KI mice. FIG. 7F presents data summary of heart rate (Paired t-test; P=0.004, n=7 mice) and PR interval (Paired t-test; P=0.0041, n=7) in CASQ2 KO mice at rest.

FIG. 8A presents representative ECG recording following intraperitoneal injection of vehicle (upper) and 20 mg/kg TRAM-34 (lower) in WT mice during treadmill exercise. TRAM-34 produced bradycardia (PP) and prolongation of the PR interval (grey arrows). FIG. 8B presents data summary of heart rate (Paired t-test; *P=0.001, n=10) and PR interval (Paired t-test; *P=0.0005, n=10) in WT mice during exercise.

FIG. 8C presents representative ECG recording following IP injection of vehicle (upper) and 20 mg/kg TRAM-34 (lower) in CASQ2-D307H KI mice during treadmill exercise. TRAM-34 produced bradycardia and markedly reduced arrhythmic features such as ventricular tachycardia. FIG. 8C presents data summary of heart rate (Paired t-test; *P=0.0004, n=11) and PR interval (Paired t-test; P=0.0099, n=9) in CASQ2-D307H KI mice during exercise.

FIG. 8E presents representative ECG recording following IP injection of vehicle (upper) and 20 mg/kg TRAM-34 (lower) in CASQ2 KO mice during exercise. Arrhythmias such as NSVT were suppressed by TRAM-34 injection. FIG. 8F presents data summary of heart rate (Paired t-test; *P=0.0165, n=7) and PR interval (Paired t-test; **P=0.0042, n=7) in CASQ2 KO mice during exercise.

FIG. 9A presents representative ECG recording following IP injection of vehicle (upper) and 20 mg/kg clotrimazole (lower) in CASQ2-D307H KI mice at rest. Clotrimazole produced bradycardia and markedly reduced arrhythmic features such as ventricular premature complexes. FIG. 9B presents data summary of heart rate (Paired t-test; *P=0.0260, n=7) and PR interval (n=7) in CASQ2-D307H KI mice at rest.

FIG. 9C presents representative ECG recording following IP injection of vehicle (upper) and 20 mg/kg clotrimazole (lower) in CASQ2 KO mice at rest showing that clotrimazole produced similar effects as in CASQ2-D307H KI mice. FIG. 9D presents data summary of heart rate (Paired t-test; **P=0.0078, n=7) and PR interval (Paired t-test; *P=0.0111, n=7) in CASQ2 KO mice at rest.

FIG. 10A presents representative ECG recording following IP injection of vehicle (upper) and 20 mg/kg clotrimazole (lower) in CASQ2-D307H KI mice during treadmill exercise. Clotrimazole changed the non-sustained ventricular tachycardia (NSVT) into ventricular premature complex (VPC). FIG. 10B presents data summary of heart rate (Paired t-test; **P=0.004, n=7) and PR interval (Paired t-test; *P=0.0305, n=7) in CASQ2-D307H KI mice during treadmill exercise.

FIG. 10C presents representative ECG recording following IP injection of vehicle (upper) and 20 mg/kg clotrimazole (lower) in CASQ2 KO mice during exercise. Typical arrhythmic features such as NSVT were improved by clotrimazole treatment. FIG. 10D presents data summary of heart rate (Paired t-test; **P=0.0037, n=7) and PR interval (Paired t-test; *P=0.0394, n=6) in CASQ2 KO mice during exercise.

TRAM-34 (20 mg/kg, IP) significantly decreased the resting heart rate of WT mice by 16±3% as measured by the PP interval (FIGS. 7A-B). A significant prolongation of 20% in the PR interval was also seen on the ECG traces of WT mice (FIGS. 7A-B). TRAM-34 produced similar bradycardic effects and PR interval prolongation during treadmill exercise of WT mice (FIGS. 8A-B).

The SK4 channel blocker clotrimazole (20 mg/kg, IP) significantly reduced the resting heart rate by 16±6% and prolonged by 27% the PR interval (data not shown). A similar trend was noticeable during treadmill exercise (data not shown).

CASQ2-D307H KI and CASQ2 KO mice displayed lower basal heart rates compared to WT mice but also irregular sinus rhythm and ventricular premature complexes as shown on the ECG traces (FIGS. 7C-D). TRAM-34 injection (20 mg/kg, IP) to these mice produced like in WT animals significant bradycardic effects (FIGS. 7E-F; 24±4% and 34±7% heart rate decrease in 12 KI and 7 KO mice respectively; p<0.005) and PR prolongation (KI mice: 23%; P=0.0001, n=12; KO mice: 46%; P=0.0041, n=7). TRAM-34 injection improved the ECG arrhythmic features observed under resting conditions and totally suppressed them in 9 out of 12 KI mice.

During treadmill exercise, the ECG cardiac abnormalities were aggravated with "non-sustained" and even "sustained" ventricular tachycardia (FIGS. 8C and 8E). Under these conditions, TRAM-34 injection decreased the prevalence and severity of arrhythmias (see, Table 1).

During treadmill exercise, TRAM-34 also produced significant sinus bradycardia and PR interval prolongation in KI and KO mice (FIGS. 8C-F).

Clotrimazole (20 mg/kg, IP) elicited similar effects to those observed with TRAM-34. Under basal conditions (FIGS. 9A-D) and during treadmill exercise (FIGS. 10A-D), bradycardia and PR prolongation were noticed in CASQ2-D307H KI and CASQ2 KO mice following clotrimazole injection. Clotrimazole improved the ECG arrhythmic features observed at rest and following treadmill exercise and even succeeded to convert them to normal sinus rhythm in 3 out of 5 KI mice and 4 of out 6 KO mice at rest (See, FIGS. 9A-D and 10A-D and Table 1).

The types of arrhythmic features were classified following their seriousness: sinusal rhythm (normal), ventricular premature contractions (VPC), non-sustained ventricular tachycardia (NSVT) and sustained ventricular tachycardia (SVT). For each mouse was considered the most severe form of arrhythmia recorded under ECG. Table 1 below presents the arrhythmogenic features at rest or during exercise in CPVT2 CASQ2-D307H KI and CASQ2 KO mice after IP injection of the SK4 blockers TRAM-34 or Clotrimazole.

TABLE 1

|  | Vehicle | Clotrimazole 20 mg/kg | Vehicle | TRAM-34 20 mg/kg |
|---|---|---|---|---|
| KI at rest |  |  |  |  |
| Number of mice (n) | 5 | 5 | 12 | 12 |
| Normal | 0 | 3 | 3 | 9 |
| VPC | 4 | 2 | 6 | 3 |
| NSVT | 1 | 0 | 3 | 0 |
| SVT | 0 | 0 | 0 | 0 |
| KI during Exercise |  |  |  |  |
| Number of mice (n) | 5 | 5 | 12 | 12 |
| Normal | 0 | 0 | 1 | 4 |
| VPC | 1 | 2 | 2 | 4 |
| NSVT | 4 | 2 | 9 | 4 |
| SVT | 0 | 1 | 0 | 0 |
| KO at rest |  |  |  |  |
| Number of mice (n) | 6 | 6 | 6 | 6 |
| Normal | 0 | 4 | 1 | 6 |
| VPC | 4 | 2 | 5 | 0 |
| NSVT | 2 | 0 | 0 | 0 |
| SVT | 0 | 0 | 0 | 0 |
| KO during exercise |  |  |  |  |
| Number of mice (n) | 6 | 6 | 6 | 6 |
| Normal | 0 | 0 | 0 | 3 |
| VPC | 0 | 2 | 0 | 0 |
| NSVT | 5 | 3 | 3 | 3 |
| SVT | 1 | 1 | 3 | 0 |

As it can be seen in Table 1, the number of mice suffering from severe forms of arrhythmia under IP vehicle injection was decreased following treatments with the SK4 blockers clotrimazole and TRAM-34 both at rest and following exercise.

Example 6

Concluding Remarks

The data presented herein demonstrate the pivotal role of SK4 $Ca^{2+}$-activated $K^+$ channels in adult pacemaker function, making them promising therapeutic targets for the treatment of cardiac ventricular arrhythmias such as CPVT and other cardiac disorders.

The results presented herein clearly identify the SK4/$IK_{Ca}$ channel as a therapeutic target involved in the adult cardiac pacemaker mechanism.

The results presented herein show that the SK4 blockers clotrimazole and TRAM-34 exhibit a bradycardic effect, while elongating the PP interval and the refractory period between two heartbeats (effect in the Atrioventricular node manifested by an increase of the PR interval), like β1-adrenergic or $Ca^{2+}$ channel blockers. This effect was demonstrated at the cellular level in human and mice cardiac cells and also in vivo.

The data presented herein primarily provide the first evidence that SK4 channels are not only expressed in spontaneously beating hESC-CMs and hiPS-CMs but in SAN cells too. Inhibition of SK4 $K^+$ currents by TRAM-34 reduced the intrinsic SAN firing rate. These data reveal that in SAN cells SK4 channels are novel regulators of mouse SAN automaticity.

Cardiac automaticity is achieved by the integration of voltage-gated currents ("membrane clock") with rhythmic $Ca^{2+}$ release from internal $Ca^{2+}$ stores ("$Ca^{2+}$ clock"). See, e.g., Brown, H. F. Electrophysiology of the sinoatrial node. Physiol Rev 62, 505-530 (1982). SAN pacemaker activity is due to the ability to generate DD, where a cohort of inward currents slowly depolarize the membrane potential until reaching the threshold of a next action potential (AP) mainly triggered by opening of voltage-gated $Ca^{2+}$ channels. These include funny currents ($I_f$), T-type $Ca^{2+}$ currents and the $Na^+$/$Ca^{2+}$ exchanger NCX1 that is activated in its forward mode by cyclical SR $Ca^{2+}$ release via RyR232,39. Outward $K^+$ currents can affect very differently murine SAN excitability. While IKR, SK2 and Ito repolarize AP, IKACh (GIRK4) can act during DD to dampen SAN firing rate [Mangoni, M. E. & Nargeot, J. Physiol Rev 88, 919-982 (2008); Li, N., et al. J Physiol 587, 1087-1100 (2009). Mahida, S. Heart Rhythm 11, 1233-1238 (2014); Xu, Y., et al. J Biol Chem 278, 49085-49094 (2003)].

The data presented herein clearly indicate that SK4 channels do not significantly alter AP duration but affect the MDP and the DD slope. In all SK channels, activation results from $Ca^{2+}$ binding to calmodulin followed by conformational changes that open the pore. The time constant ($\tau$=5 ms) of this activation process is strongly dependent on intracellular $Ca^{2+}$. SK channel deactivation, initiated by dissociation of $Ca^{2+}$, is independent of intracellular $Ca^{2+}$ and occurs on a much slower time scale ($\tau$=15-60 ms). SK channels can remain active for more than 100 ms after $[Ca^{2+}]i$ has returned to resting levels. See, for example, Berkefeld et al. *Physiol Rev* 90, 1437-1459 (2010).

Because of this slow channel deactivation, it has been suggested herein that SK4 channel contribution becomes significant only at the late repolarization, thereby contributing to the MDP hyperpolarization, which facilitates activation of $I_f$ and recovery from inactivation of voltage-gated $Ca^{2+}$ channels. Thus, the net effect of SK4 channel activation is an increase in the firing rate. SK4 channels may act in SAN like BKCa channels in hippocampal neurons, where their activation counterintuitively increases excitability, while their inhibition reduces firing.

The in vitro and in vivo data obtained with the SK4 channel blockers, TRAM-34 and clotrimazole, on the pacing rate of isolated SAN cells and on ECG parameters of WT mice, as presented herein, indicate that activation of SK4 channels increases the SAN pacing rate and their blockade reduces it. Both blockers produced significant bradycardic effects during rest and following treadmill exercise. An indirect impact of TRAM-34 or clotrimazole on autonomic input to SA and AV nodes in vivo can be excluded because both blockers exert similar effects on isolated SAN cells. In line with these data, RA-2, a structurally different molecule from TRAM-34 and clotrimazole, with a mixed blocker activity toward SK4 and SK2 channels, induced bradycardia in mice, an effect abolished in SK4 knockout mice [Olivan-Viguera, A., et al. *Mol Pharmacol* 87, 338-348 (2015)]. The prolongation of the PR interval is related to either AV node and/or the HisPurkinje system and suggests that SK4 channels are likely expressed in the conduction system.

Previous transcriptional analysis showed a 9-fold upregulation of SK4 in the developing conduction system compared to SK1-346. Reflecting functional redundancy among SAN ionic conductances, it is noted that additional $Ca^{2+}$-activated $K^+$ channels have been characterized in the murine cardiac pacemaker. Blockade of SK2 channels prolonged the AP duration in atrioventricular nodal cells and knockout of SK2 channels in mice resulted in bradycardia and prolongation of the PR interval. Conversely, overexpression of SK2 channels decreased AP duration, increased spontaneous firing rate of atrioventricular nodal cells and reduced PR and RR intervals in ECG. See, for example, Zhang, Q., et al. *Circ Res* 102, 465-471 (2008)]. More recently, $Ca^{2+}$- and voltage-activated BK $K^+$ channels were also identified in murine SAN cells. Genetic ablation or pharmacological inhibition of BK channels were associated with reduced heart rate in ECG and slowed SAN cells pacing without alteration of AP duration. See, for example, Lai, M. H., et al. *Am J Physiol Heart Circ Physio* 307, H1327-1338 (2014)]. This apparent redundancy of $Ca^{2+}$-activated $K^+$ currents indicates that they share similar properties such as bradycardia upon channel blockade (SK2, SK4 and BK) but they also exhibit subtle differences notably regarding their impact on AP duration (e.g., SK2 versus SK4).

The data presented herein show that inhibition of SK4 $K^+$ channels rescues in vitro the cardiac arrhythmias exhibited by hiPS-CMs derived from CPVT2 patients carrying the CASQ2 D307H mutation and by SAN cells isolated from CASQ2-D307H KI mice. Hence, TRAM-34 markedly reduced the occurrence of DADs and abnormal $Ca^{2+}$ transients detected following exposure to the β-adrenergic agonist isoproterenol. SK4 channel blockers can therefore protect in vivo the animals from deleterious ventricular arrhythmic features revealed by ECG in CASQ2-D307H KI and CASQ2 KO mice at rest and after treadmill exercise.

Ventricular premature complexes, non-sustained and sustained ventricular tachycardia were significantly reduced following a single IP injection (20 mg/kg) of clotrimazole or TRAM-34. The SK4 channel blockers protected the CASQ2-D307H KI and CASQ2 KO mice from harmful polymorphic ventricular tachycardia without being pro-arrhythmic by themselves, since neither sinus arrest nor 2nd order AV block were recorded in the animals, including WT mice.

Despite the blockade of SK4 channels, the functional redundancy of $Ca^{2+}$-activated $K^+$ channels likely preserves the delicate balance of inward and outward currents necessary for normal pacemaking. Along the same line, recent studies showed that cardiac SAN arrhythmias induced by silencing either HCN4 ($I_f$ current) or Cav1.3 (L-type $Ca^{2+}$ currents) could be rescued by genetic deletion or pharmacological inhibition of GIRK4 channels (IKACh currents) [Lai, M. H., et al. (2014), supra; Mesirca, P., et al. *Nat Commun* 5, 4664 (2014); Mesirca, P., et al. *Proc Natl Acad Sci USA* 113, E932-941 (2016)].

Due to their bradycardic effect and slowed AV conduction, SK4 channel blockers, very much like β1-adrenergic or $Ca^{2+}$ channel blockers, are beneficial for preventing ventricular tachycardia by prolonging the refractory period.

These data indicate that the therapeutic indications of SK4 channel blockers could be extended to non arrhythmic cardiovascular disorders, ventricular tachyarrhythmias in CPVT and possibly in other arrhythmic pathologies of different etiologies such as the long QT syndrome.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of treating Catecholaminergic polymorphic ventricular tachycardia (CPVT) in an adult subject in need thereof, the method comprising administering to the subject a blocker of a SK4 channel, wherein administering said blocker of a SK4 channel results in elongating or prolonging a PR interval of the subject, thereby preventing ventricular tachycardia in the subject.

2. The method of claim 1, wherein said subject is a human subject.

3. The method of claim 1, wherein said SK-4 channel blocker forms a part of a pharmaceutical composition which further comprises a carrier.

\* \* \* \* \*